US012180446B2

(12) United States Patent
Huh et al.

(10) Patent No.: US 12,180,446 B2
(45) Date of Patent: Dec. 31, 2024

(54) NATIVE EXTRACELLULAR MATRIX-DERIVED MEMBRANE INSERTS FOR ORGANS-ON-CHIPS, MULTILAYER MICROFLUIDICS MICRODEVICES, BIOREACTORS, TISSUE CULTURE INSERTS, AND TWO-DIMENSIONAL AND THREE-DIMENSIONAL CELL CULTURE SYSTEMS

(71) Applicant: THE TRUSTEES OF THE UNIVERSITY OF PENNSYLVANIA, Philadelphia, PA (US)

(72) Inventors: Dongeun Huh, Villanova, PA (US); Mark Mondrinos, Philadelphia, PA (US); Alex Yoon Yi, Philadelphia, PA (US); Jeongyun Seo, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 31 days.

(21) Appl. No.: 16/787,275

(22) Filed: Feb. 11, 2020

(65) Prior Publication Data
US 2020/0190456 A1    Jun. 18, 2020

Related U.S. Application Data

(63) Continuation of application No. PCT/US2018/046479, filed on Aug. 13, 2018.
(Continued)

(51) Int. Cl.
*C12M 3/06* (2006.01)
*C12M 1/00* (2006.01)

(52) U.S. Cl.
CPC ............ *C12M 23/16* (2013.01); *C12M 23/22* (2013.01); *C12M 23/34* (2013.01); *C12M 29/04* (2013.01); *C12M 29/10* (2013.01)

(58) Field of Classification Search
CPC ...... C12M 23/16; C12M 23/22; C12M 23/34; C12M 29/04; C12M 29/10
See application file for complete search history.

(56) References Cited

U.S. PATENT DOCUMENTS 3,199,547 A     8/1965  Knutson et al.
5,326,265 A     7/1994  Prevou
(Continued)

FOREIGN PATENT DOCUMENTS

WO       2016/154319 A1      9/2016
WO       WO-2017008035 A1 *  1/2017  ............. A61K 35/42
WO       WO-2020073043 A1 *  4/2020  ........ B01L 3/502707

OTHER PUBLICATIONS

Lee et al. "Placenta-on-a-chip: a novel platform to study the biology of the human placenta". J Matern Fetal Neonatal Med, 2016; 29(7): 1046-1054. (Year: 2015).*
(Continued)

*Primary Examiner* — Michael L Hobbs
(74) *Attorney, Agent, or Firm* — BakerHostetler

(57) ABSTRACT

The presently disclosed subject matter provides native extracellular matrix-derived membrane inserts for organs-on-chips, multilayer microfluidics microdevices, bioreactors, tissue culture inserts, and two-dimensional and three-dimensional cell culture systems. A microfluidic cell culture is provided that can include at least one membrane including extracellular matrix (ECM) material. The ECM material can be used to construct a perfusable microfluidic system including a plurality of layers of microfabricated cell culture chambers. The microfluidic cell culture can further include a lower layer including a microchannel on which the at least (Continued)

one membrane is placed and an upper layer including another microchannel. The upper layer can be bonded to the lower layer.

23 Claims, 31 Drawing Sheets

Related U.S. Application Data

(60) Provisional application No. 62/544,429, filed on Aug. 11, 2017.

(56) References Cited

U.S. PATENT DOCUMENTS

| | | | |
|---|---|---|---|
| 2005/0074875 A1* | 4/2005 | Nigam | A61K 38/1825 |
| | | | 435/366 |
| 2005/0129720 A1 | 6/2005 | Takezawa et al. | |
| 2010/0028624 A1 | 2/2010 | Smith et al. | |
| 2011/0250585 A1* | 10/2011 | Ingber | C12N 5/0623 |
| | | | 435/5 |
| 2013/0040114 A1 | 2/2013 | Culler et al. | |
| 2014/0038279 A1* | 2/2014 | Ingber | C12M 23/38 |
| | | | 435/297.2 |
| 2014/0242355 A1 | 8/2014 | Castille | |
| 2014/0349332 A1* | 11/2014 | Yasuda | G01N 33/5061 |
| | | | 435/29 |
| 2015/0017140 A1 | 1/2015 | Bhatia et al. | |
| 2017/0088807 A1* | 3/2017 | Kim | C12M 23/34 |
| 2020/0055054 A1* | 2/2020 | Hajipouran Benam | |
| | | | C12M 23/16 |
| 2021/0371792 A1* | 12/2021 | Takeuchi | C12M 25/04 |

OTHER PUBLICATIONS

International Search Report mailed Oct. 30, 2018 in International Application No. PCT/US2018/048625.
Su et al., "Ultra-high cooling rate utilizing thin film evaporation" Applied Physics Letters, vol. 101,Sep. 10, 2012, pp. 1-3, 113702.
Wikipedia, "Decellularization", retrieved from https://en.wikipedia.org/w/index.php?title=Decellularization&oldid=711141048, Mar. 21, 2016, retrieved on Oct. 15, 2018.
Wikipedia, "Extracellular matrix", retrieved from https://en.wikipedia .org/w/index.php?title=Extracellular_matrix&oldid=748378091, Nov. 7, 2016, retrieved on Oct. 15, 2018.

* cited by examiner

Bonding

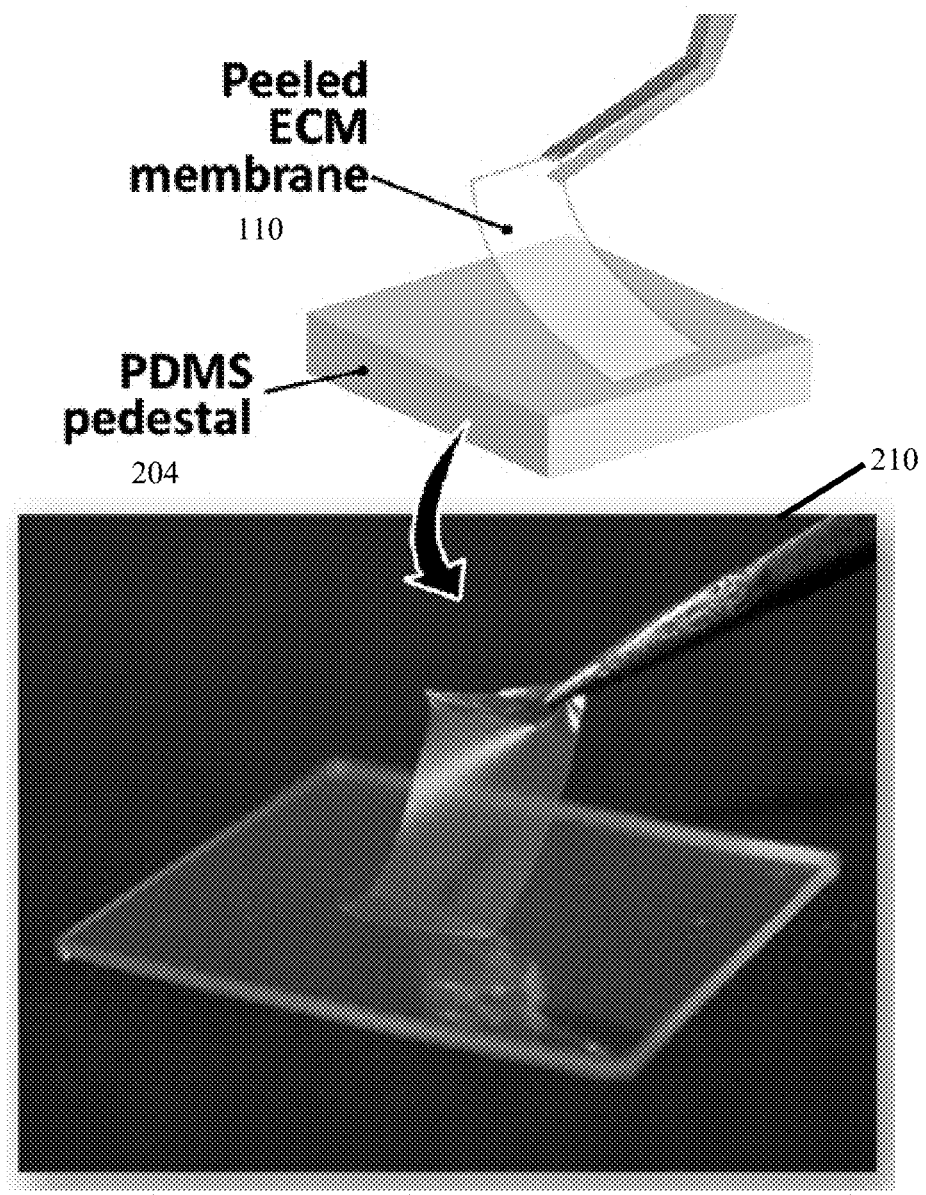

NATIVE EXTRACELLULAR MATRIX-DERIVED MEMBRANE INSERTS FOR ORGANS-ON-CHIPS, MULTILAYER MICROFLUIDICS MICRODEVICES, BIOREACTORS, TISSUE CULTURE INSERTS, AND TWO-DIMENSIONAL AND THREE-DIMENSIONAL CELL CULTURE SYSTEMS

CROSS REFERENCE TO RELATED APPLICATION

This application is a continuation of International Application No. PCT/US2018/046479, filed Aug. 13, 2018, which claims priority to U.S. Provisional Application No. 62/544,429, filed Aug. 11, 2017, the contents of each of which are incorporated by reference herein.

STATEMENT REGARDING FEDERALLY SPONSORED RESEARCH

This invention was made with government support under the Director's New Innovator Award 1DP2HL127720-01 awarded by the National Institutes of Health (NIH). The government has certain rights in the invention.

BACKGROUND

Recapitulating native three-dimensional (3D) organ microenvironments is a challenge in the development of biomimetic models of human physiology and disease. Microenvironmental cues such as local architecture, mechanical forces, and biochemical signals can define the physiological, or pathological situation in vivo.

Microphysiological cell culture models, collectively known as organs-on-chips, are rapidly emerging as a popular platform to emulate the essential units of living organs for a wide variety of applications. By enabling new capabilities to present cultured cells with physiologically relevant structural, biochemical, and biomechanical cues, certain organ-on-a-chip models can mimic the native phenotype of various tissue types and their integrative behaviors that give rise to complex organ-level functions.

Construction of certain microphysiological models often requires perfusable microfluidic systems that consist of stacked layers of microfabricated cell culture chambers. This design provides a compartmentalized environment advantageous for co-culture of different cell types to replicate cellular heterogeneity and multilayered tissue structures found in virtually all organs. As a key component in this type of microdevices, semipermeable membranes containing nanoscale sized or microscopic pores are commonly used as cell culture substrates sandwiched between two adjacent chambers. In this configuration, the membranes provide a physical barrier to cell migration and enable the compartmentalization of different cell populations while permitting their exchange of soluble signaling molecules through the pores, recapitulating the role of the basement membrane in vivo. This approach has been used in certain microengineered cell culture models to reconstitute various types of tissue-tissue interfaces and to study their physiological functions in a range of contexts. Despite the considerable progress in this area, existing models that commonly use synthetic cell culture substrates still suffer from the lack of ability to recapitulate the interaction of cells with their surrounding extracellular matrices such as the basement membrane.

A lack of cell culture substrates that mimic the native extracellular matrix (ECM) remains a significant problem not only for organ-on-chip models but also for various types of bioreactors, tissue culture inserts, and 3D in vitro cell culture systems. The ECM, which can serve as both a structural scaffold and cell adhesion substrate, possesses a tissue-specific composition and topology that can instruct diverse processes including growth, differentiation, and tissue morphogenesis/remodeling. ECM is an insoluble component of the cellular microenvironment and serves as the anchorage substrates for the cells by engaging ECM ligand-specific cell surface receptors. Certain available 3D cell culture systems, bioreactors, and in vitro tissue culture platforms do not provide a mechanism to support cell-ECM interactions and instead these currently available systems use a synthetic membrane support. Accordingly, there remains a need to be able to control the spatial geometry, microarchitecture, composition, and optical and biomechanical properties of the ECM materials in various types of cell culture systems in order to develop physiologically relevant in vitro models that can recapitulate and predict essential in vivo structure and function of living tissues and organs.

BRIEF DESCRIPTION OF THE FIGURES

FIGS. 2A-2F are images illustrating the appearance, surface structure, and composition of the ECM-derived membranes in accordance with an exemplary embodiment of the disclosed subject matter.

Figure 1A:
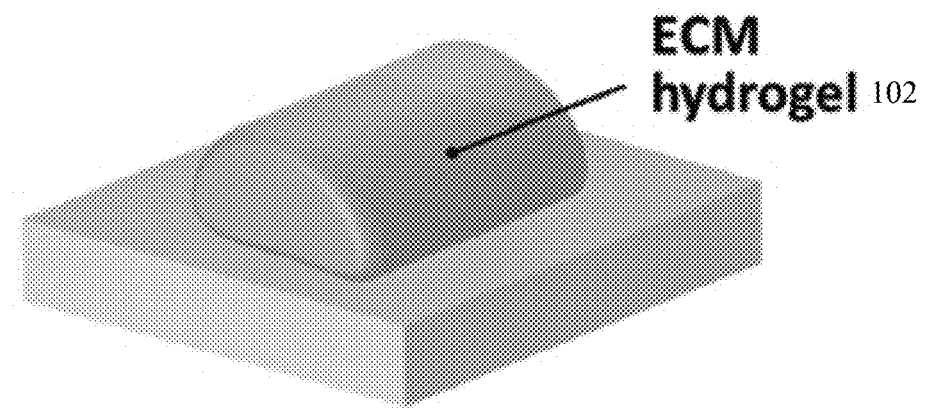
FIGS. 1A-1J are diagrams illustrating an exemplary technique for fabricating ECM-derived membrane inserts for microfluidic cell cultures in accordance with an exemplary embodiment of the disclosed subject matter.

Throughout the drawings, the same reference numerals and characters, unless otherwise stated, are used to denote like features, elements, components or portions of the illustrated embodiments. Moreover, while the present disclosed subject matter will now be described in detail with reference to the figures, it is done so in connection with the illustrative embodiments.

DETAILED DESCRIPTION

Semipermeable cell culture membranes are commonly used in multilayered microfluidic devices to mimic the basement membrane in vivo and to create compartmentalized microenvironments for physiological cell growth and differentiation. The presently disclosed subject matter provides a novel type of cell culture membranes engineered from native extracellular matrix (ECM) materials that can be thin, semipermeable, optically transparent, and amenable to integration into microfluidic cell culture devices.

Facile and cost-effective fabrication of these membranes can be achieved by controlled sequential procedures of vitrification that transformed three-dimensional (3D) ECM hydrogels into structurally stable thin films. By modulating the composition of the ECM, disclosed techniques can provide a means to tune key membrane properties such as optical transparency, stiffness, and porosity. For microfluidic cell cultures, the disclosed subject matter provides a multi-layered microdevice consisting of two parallel chambers separated by a thin membrane insert derived from different types of ECM. The disclosed ECM membranes can support attachment and growth of various types of cells (e.g., epithelial, endothelial, and mesenchymal cells) under perfusion culture conditions. The disclosed subject matter can enable the promotive effects of the membranes on adhesion-associated intracellular signaling that mediates cell-ECM interactions. Furthermore, the disclosed membranes can be used for constructing compartmentalized microfluidic cell culture systems to induce physiological tissue differentiation or to replicate interfaces between different tissue types. The disclosed subject matter can provide a robust platform to produce and engineer biologically active cell culture substrates that serve as viable alternatives to conventional synthetic membrane inserts. The disclosed subject matter can contribute to the development of physiologically relevant in vitro cell culture models for a wide range of applications.

Microphysiological cell culture models, collectively known as organs-on-chips, are rapidly emerging as a novel platform to emulate the essential units of living organs for a wide variety of applications. By enabling new capabilities to present cultured cells with physiologically relevant structural, bio-chemical, and biomechanical cues, organ-on-a-chip models can mimic the native phenotype of various tissue types and their integrative behaviors that give rise to complex organ-level functions. This biomimetic microengineering technique can be used to model the functional units of various organs for basic and translational research.

Construction of microphysiological cell culture models can require perfusable microfluidic systems having stacked layers of microfabricated cell culture chambers. In some embodiments, such a design can provide a compartmentalized environment advantageous for co-culture of different cell types to replicate the cellular heterogeneity and multi-layered tissue structures found in virtually all organs. Semipermeable membranes containing nano-sized and/or microscopic pores can be commonly used as cell culture substrates sandwiched between two adjacent chambers. In this configuration, the membranes can provide a physical barrier to cell migration and can enable the compartmentalization of different cell populations while permitting their exchange of soluble signaling molecules through the pores, mimicking the role of the basement membrane in vivo. Such techniques can be used to reconstitute various types of tissue-tissue interfaces and to study their physiological functions in a range of contexts including immune responses, biomolecular transport, gas and fluid exchange, drug delivery, and nanoparticle absorption.

Existing selections of commercially available and/or custom-designed semipermeable membranes suffer from several limitations. Most notably, certain cell culture membranes in use today are made up of synthetic polymers, such as polyesters, polycarbonates, or poly-dimethylsiloxane) (PDMS), which can significantly differ from native ECM. ECM can provide an insoluble component of the cellular microenvironment and can serves as an anchorage substrate for adherent cells by engaging ECM ligand-specific cell surface receptors. To mimic this aspect of cell-ECM interactions, synthetic membranes can be modified by absorptive coating or covalent bonding of ECM proteins on the surface to support cell attachment. However, the bulk material of synthetic membranes remains foreign and fails to mimic the biochemical composition of the basement membrane that provides instructive cues for expression of physiological the ability to mimic the fibrous architecture and physical properties (e.g. stiffness) of native matrices that influence the structure and function of cells.

These inherent limitations of existing membranes often become the cause discrepancies between microphysiological models and their in vivo counterparts. Furthermore, the lack of optical transparency is another common problem in certain types of synthetic membranes (e.g., electrospun substrates, microporous Transwell inserts) that imposes constraints on imaging and analysis of cells in membrane-containing microfluidic devices. In addition, the fabrication of porous membranes demands specialized and expensive manufacturing techniques such as track etching, electrospinning, and chemical etching. Such specialized fabrication requirements can present a major practical challenge for routine production and optimization of cell culture membranes necessary for rapid-prototyping microphysiological systems in a research laboratory environment.

In an effort to address these problems, the presently disclosed subject matter can provide a simple and cost-effective strategy to generate semipermeable cell culture membranes and thin substrates derived from native ECM proteins that can be easily integrated into microfabricated devices. These ECM-derived natural materials can be used in other types of in vitro cell culture systems such as bioreactors, Transwell-type tissue culture inserts, and hydrogel-based 3D cell culture models, to name a few examples. This technique utilizes natural evaporation-driven dehydration and vitrification of ECM hydrogel scaffolds to form thin ECM films without requiring specialized equipment or infrastructure. The resulting membranes can be fibrous, clear, permeable, and mechanically stable enough to retain their structural integrity during bonding and assembly of multi-layered microfluidic devices. In some embodiments, by using collagen hydrogel and Matrigel as representative materials, the disclosed subject matter can provide new capabilities to tune the properties of ECM membranes and to modulate the attachment and organization of different types of adherent cells. Furthermore, the disclosed membranes can be used in compartmentalized microdevices to engineer living human barrier tissues that resemble various types of tissue-tissue interfaces in vivo. The disclosed naturally derived membranes can offer new opportunities to overcome the major limitations of conventional semipermeable membranes and to improve the physiological relevance and predictive capacity of microfluidic cell culture models.

In some embodiments, using ECM can provide an approach to engineer active cell culture substrates that are more physiologically relevant for a variety of in vitro cell culture models. An ECM substrate can have a role in tissue engineering 2D or 3D scaffolding. In some embodiments, ECM can be a component of an organ-on-chip system. In some other embodiments, the ECM can serve as a stand-alone additive for organ-on-chip systems. The ECM can provide a biologically active substrate able to induce pathological and physiological responses in a programmable fashion. In some embodiments, ECM can help simulate an actual micro-biosystem for evaluating an organ on chip system. In some embodiments, ECM can be used as a foundational material for organ-on-chip systems. In some embodiments, ECM can be used as a substrate for cell culture bioreactors. In some embodiments, ECM can be incorporated into a tissue-culture insert (e.g., Transwell). In some embodiments, ECM can serve as a structural and functional scaffold for 3D tissues. In some embodiments, ECM can be used as a stand-alone structure for forming 2D tissue layers (e.g., cell sheets). In some embodiments, ECM can provide a naturally-derived structural scaffold for creating tubular tissue structures (e.g., blood vessels, collecting ducts, bile ducts, airways, etc.).

In some embodiments, the disclosed subject matter can provide a simple and cost-effective technique to generate new types of microfluidic cell culture membranes engineered from native ECM proteins. The disclosed ECM membranes can be semipermeable, optically transparent, tunable in their biochemical and biophysical properties, and can resemble fibrous architecture of native basement membranes. As supported by measurement data described below, the disclosed ECM membranes can be advantageous over traditional cell culture inserts and can be integrated into multilayered microfluidic devices to mimic physiological multicellular structures and tissue-tissue interfaces.

In some embodiments, the disclosed membranes can be fabricated using ECM materials collagen type I and Matrigel. In some other embodiments, fabrication of the disclosed membranes can use ECM materials derived directly from animal or human tissue and organ sources. For example, the disclosed fabrication processes can include using decellularized tissues and organs as cell-free scaffolds composed of the native ECM as well as harvesting of these decellularized ECM (d-ECM) materials for the purposes of forming hydrogels and other 3D cell culture substrates. The disclosed subject matter describes using d-ECM for the fabrication of partitioning membrane inserts for multilayer microfluidic cell culture devices (i.e., organs-on-chips). In some embodiments, d-ECM materials that have been harvested from human cadaveric tissues can be used for membrane fabrication. In an exemplary embodiment, skeletal muscle-specific membranes can be fabricated utilizing animal-derived skeletal muscle d-ECM material. These d-ECM-derived membranes can possess general physical characteristics similar to membranes composed of type I collagen blended with Matrigel. The spectrum of skeletal muscle ECM proteins present in these membranes can be characterized and the capacity of such skeletal muscle ECM proteins can be validated to facilitate enhanced skeletal myoblast adhesion and myocyte differentiation. In some embodiments, human ECM materials for membrane fabrication can be derived from cultured human cells and engineered human microtissues.

According to another aspect of the disclosed subject matter, different methods of fabricate ECM membranes and thin tissue constructs are described herein. In some embodiments, an exemplary fabrication method can be based on natural evaporation-induced vitrification of ECM hydrogels.

In some other embodiments, the ECM membranes and/or thin yet mechanically robust ECM layers can be produced using exemplary methods including mechanical compression of hydrogels using externally applied weight or vacuum. For example, the ECM membranes can be "squeezed" to drain the gels of liquid to shrink the gels using such a compression method.

In some other embodiments, the ECM membrane and/or thin yet mechanically robust ECM layers can be created using mechanical vibration of hydrogels. In some other embodiments, similar ECM structures can be fabricated by exposure of hydrogels to certain source of thermal, electrical, magnetic, and/or optical energy. The disclosed fabrication methods can facilitate living cells to be embedded in the hydrogel and can allow the living cells to maintain their viability during the fabrication processes. In some embodiments, the geometry of the resultant tissue structures can be engineered by patterning the location of applied compression. In some embodiments, the disclosed vacuum-based compression can be significantly faster than certain weight-based compression techniques.

In some embodiments, the disclosed subject matter can provide a robust approach to engineer biologically active cell culture substrates that can serve as an alternative to conventional synthetic membrane inserts. The disclosed techniques for fabricating such biologically active cell culture substrates can be used to develop physiologically relevant in vitro cell culture models for a wide range of applications.

In some embodiments, the disclosed techniques can be used to fabricate membranes that can contain microscopic and/or nanoscopic topography. In some embodiments, the disclosed techniques can be applied to generating ECM hydrogel constructs that contain 2D and 3D structures reminiscent of tissue and organ microarchitecture seen in vivo. In some embodiments, the disclosed techniques can provide a method for producing 2D and 3D hydrogel structures for cell culture in various types of bioreactors and high-throughput cell culture platforms.

In a commercial setting, the disclosed subject matter can be translated into a product line including staple membranes comprised of commonly used ECM components such as collagens and laminins. These membranes can be purchased by the end user and integrated in multilayer microfluidic devices in their own laboratory or as part of pre-fabricated microdevice or larger integrated system. Application-specific membranes can be engineered from ECM material isolated from the tissue type of interest. For example, a skeletal muscle ECM solution, which can be typically used for forming hydrogels, can be used to engineer membrane inserts for on-chip culture of skeletal myoblasts. Biologically active membrane inserts for microfluidic cell culture can have a broad range of end-users that will only increase with time as the use of microfluidic culture platforms becomes more prevalent in numerous areas of biomedical research. In some embodiments, the disclosed subject matter can be leveraged to generate products including semi-porous membranes for tissue culture inserts (e.g., Transwell), cell culture microbeads for bioreactors, culture membranes for forming cell/tissue sheets, ECM tubes for engineering tubular tissues for cell culture and tissue engineering applications. In some embodiments, the disclosed subject matter can be used to produce commercially available cell-laden living human and animal tissues for organ repair and regeneration.

Membrane Fabrication

Figure 1B:
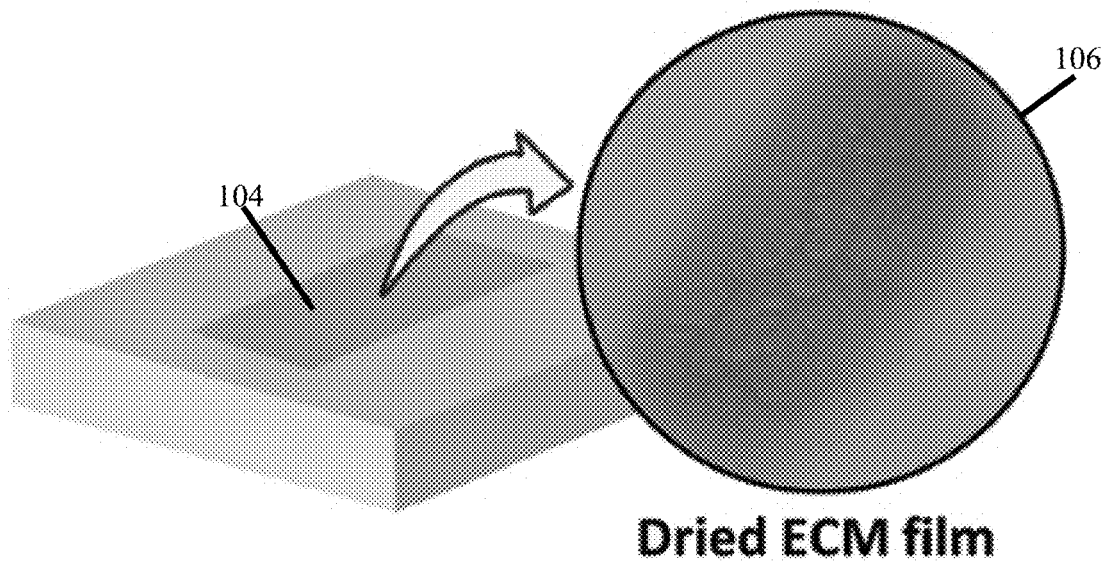
Figure 1C:
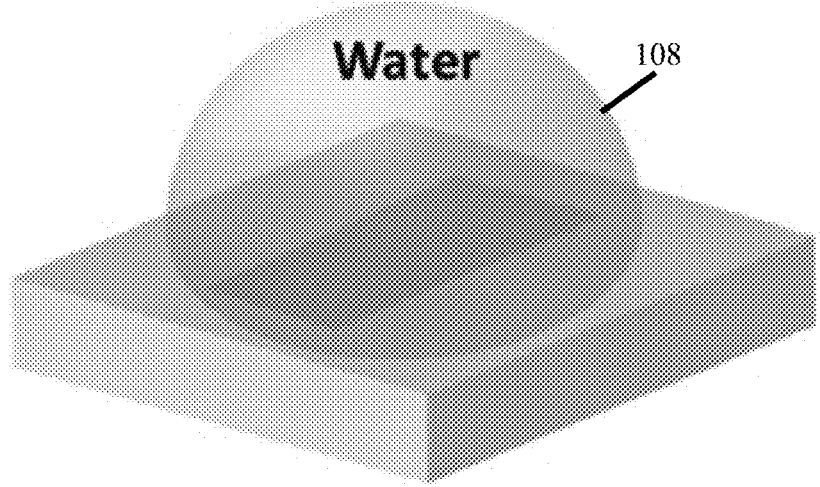
Figure 1D:
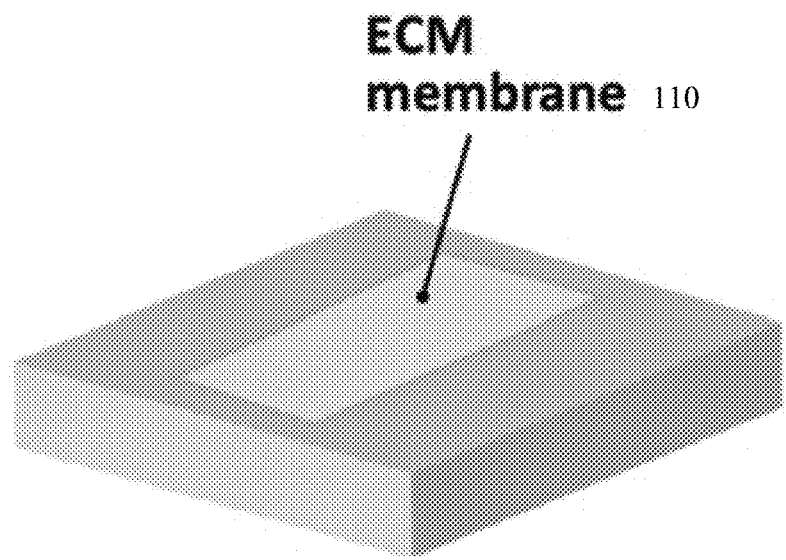
Figure 1E:
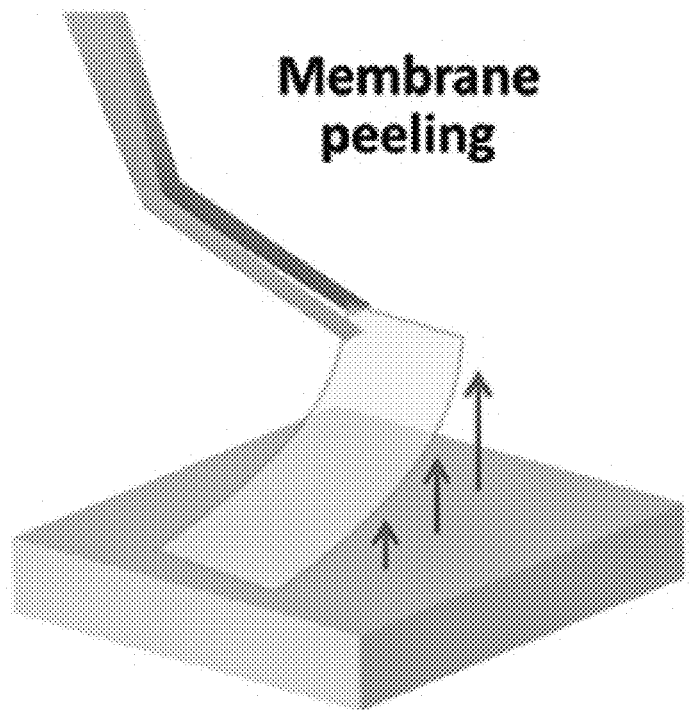

FIGS. 1A-1J are diagrams illustrating an exemplary technique for fabricating ECM-derived membrane inserts for microfluidic cell cultures. As shown in FIG. 1A, a predetermined volume of ECM hydrogel precursor solution 102 can be distributed evenly on a flat PDMS slab and incubated at 37° C. for 1 hour to allow for gelation. Subsequently, as shown in FIG. 1B, the hydrogel can be dried in a sterile environment at room temperature overnight. During this process, an evaporative loss of water content from the gel can cause a drastic volume reduction and eventually result in the formation of a thin sheet 104 on the PDMS surface that showed a color and crystallized residues as shown in the expanded inset 106 shown in FIG. 1B. As shown in FIG. 1C, the ECM film can then be rehydrated in pure distilled deionized (DDI) water 108 for 4 hours to remove salts, phenol red, and other impurities. Following gentle aspiration of water 108, the film can undergo another drying cycle to create a thin ECM membrane 110 supported by an underlying PDMS substrate as shown in FIG. 1D. Finally, as illustrated in FIG. 1E, the membrane can be peeled off from the PDMS pedestal using fine forceps and cut to the desired size and shape for use in microfluidic devices. To yield membrane strips of uniform thickness as measured, 1-2 mm of the ECM membrane can be trimmed off the edges of the ECM membranes after peeling to remove sloped boundary regions. The uniform thickness can be verified by measuring the thickness of each membrane at multiple locations using the image analysis technique described below.

Figure 1F:
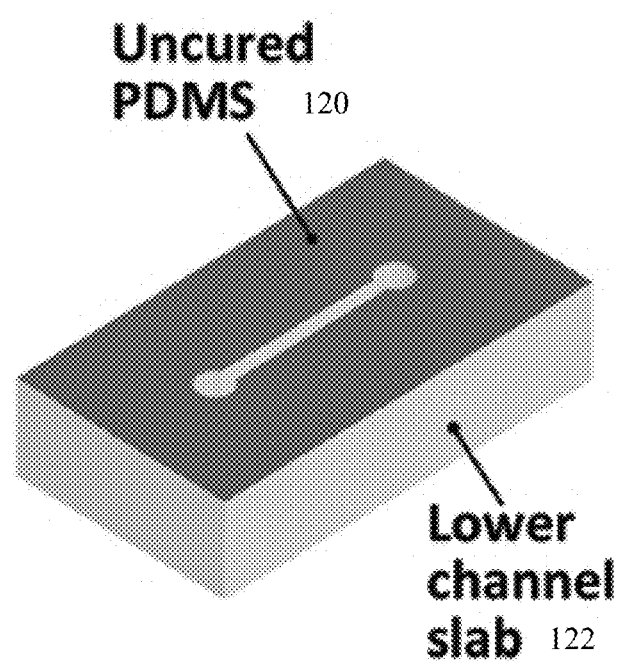
Figure 1G:
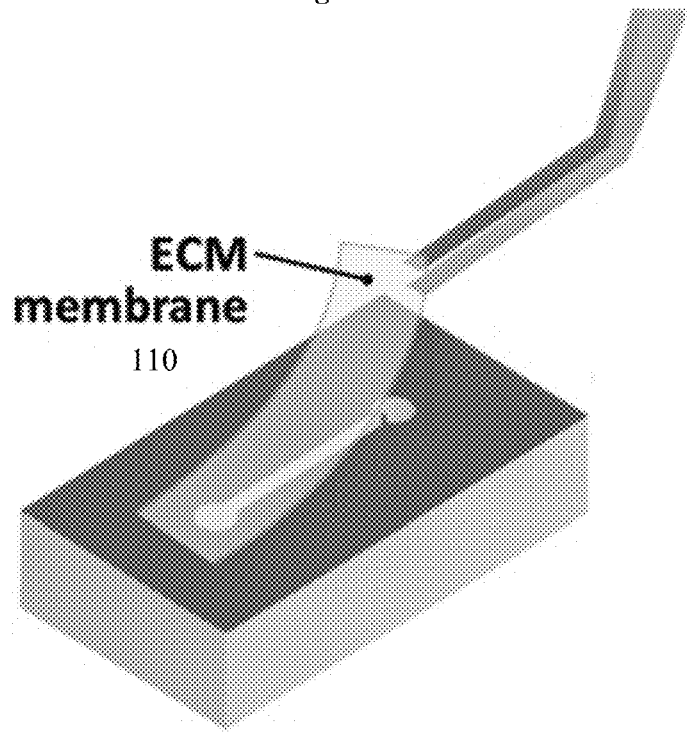
Figure 1H:
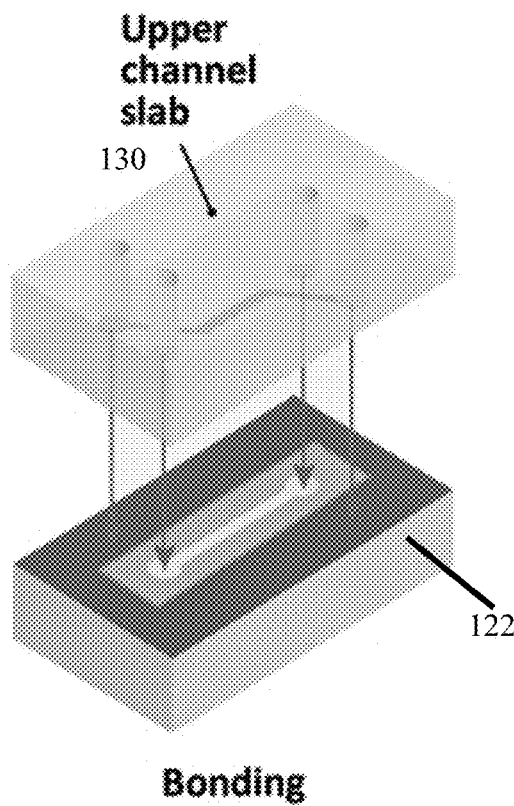
Figure 1I:
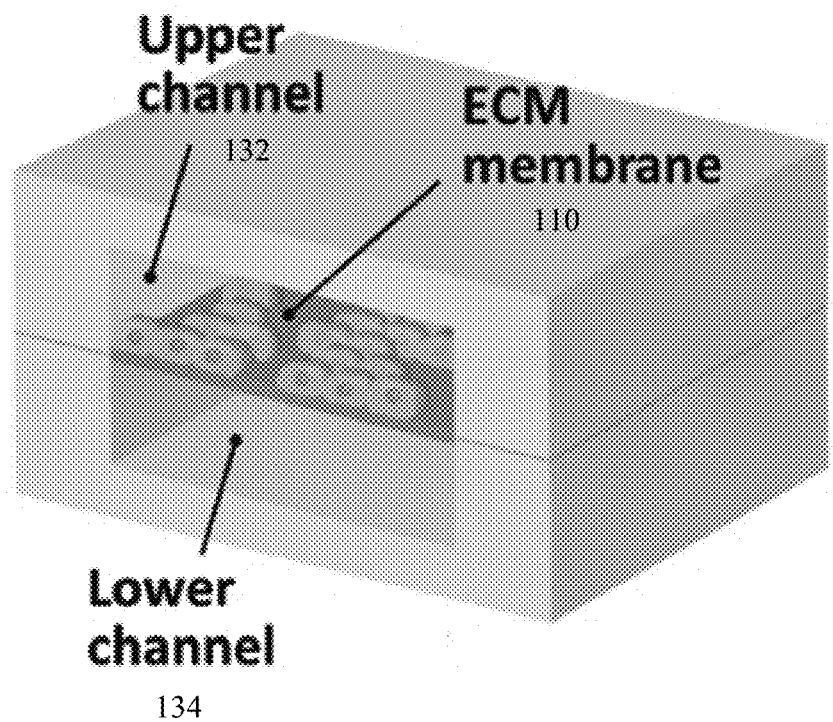
Figure 1J:
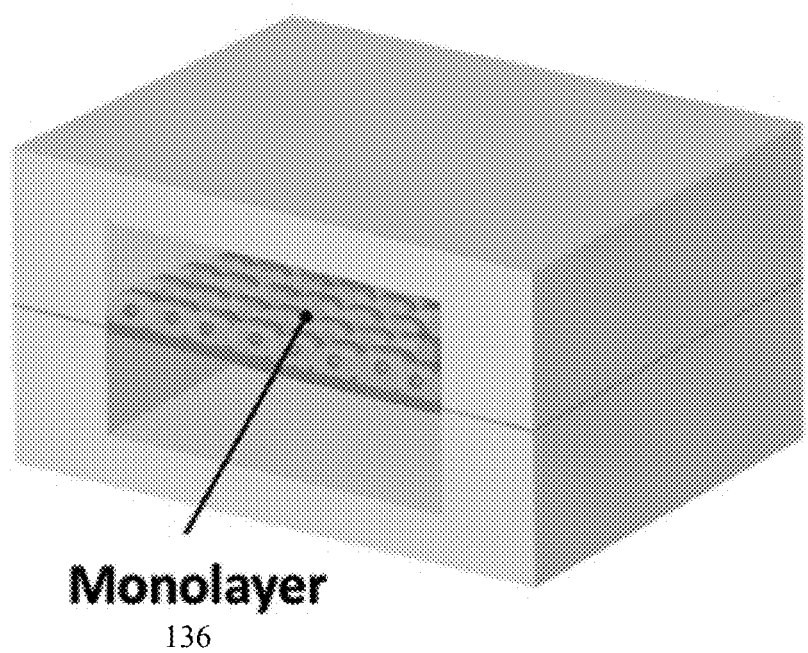

FIG. 1F illustrates microfluidic channel slabs fabricated by soft lithography that can be stamped with uncured PDMS 120 to facilitate bonding of ECM membrane inserts over microfluidic channels in the lower channel slab 122. FIG. 1G illustrates that ECM membrane 110 can be placed over the lower channel using forceps. FIG. 1H illustrates that the upper channel slab 130 can be stamped with uncured PDMS is bonded to the lower channel slab 122 to create an enclosed three-layer channel system. The cross-sectional view of the fully assembled device is shown in FIG. 1I and FIG. 1J. As shown in FIG. 1I, cells can be seeded on the ECM-derived membrane 110 inserts in microfluidic devices between the upper channel 132 and lower channel 134. As shown in FIG. 1J, during perfusion culture, the seeded cells can proliferate on the membrane surface to form stable, confluent monolayers 136 in microdevices.

Production of ECM membranes with different compositions and thicknesses

In some embodiments, three types of ECM membranes composed of i) collagen type I (COL), ii) collagen type I and Matrigel (COL-MAT), or iii) collagen type 1 and alginate (COL-ALG) can be generated. For the production of pure COL membranes, rat tail collagen type I (i.e., Corning) solution can be prepared at 2 mg ml$^{-1}$ according to the manufacturer's protocols. In some embodiments, 400 μl of this solution can be used to carry out the fabrication procedure described above. In some embodiments, to generate COL-MAT membranes, Matrigel (~10 mg ml$^{-1}$ supplied by Corning) can be mixed with 2 mg ml$^{-1}$ collagen solution at volume ratios of 1:4, 1:1, and 4:1. The remainder of the fabrication process can be identical, with the addition of incubation with 10 mU ml$^{-1}$ transglutaminase in 1×PBS solution for 2 hours at 37° C. prior to rehydration in DDI water to cross-link Matrigel components with the collagen type I matrix. In some embodiments, COL-ALG membranes can be fabricated using collagen (i.e., 2 mg ml$^{-1}$) and alginate (i.e., 10 mg ml$^{-1}$) solutions mixed at ratios of 2:1, 1:1, and 1:2 (v/v). The same fabrication procedure can be followed with the exception that the membranes can be soaked in DDI water for 2 hours at room temperature and another 2 hours at 37° C. to remove alginate used as a sacrificial material to increase the porosity of the resultant membranes.

In some embodiments, to change the thickness of our ECM membranes, sequential layering techniques can be used to generate membranes consisting of stacked layers of COL membranes. In an exemplary embodiment, the number of COL layers can range from 2 to 4 to vary the thickness of the resultant membrane. After the first layer has been formed using the aforementioned protocol, the first layer can be wetted with 10 mU ml$^{-1}$ transglutaminase solution and overlaid with the second layer to prevent air bubble formation between the layers. The layered COL membranes can be incubated for 2 hours in transglutaminase solution at 37° C., and this step can be followed by three separate washes in 1×DPBS. This can be repeated for additional layers. To measure the membrane thickness, one edge of the membrane can be sandwiched between sets of glass slides while the center of the membrane remained freely suspended. For each membrane, z-stack acquisition of 100 μm can be performed using a long working distance inverted microscope (i.e., Zeiss) at the center of the membrane. Using the ZEN software (i.e., Zeiss), an orthogonal projection can be created from the z-stack and further processed using the maximum intensity projection along the z-axis. The final image can exhibit each pixel at its maximum intensity over the entire image stack. Image analysis can be carried out using ImageJ software to quantify the membrane thickness.

Microdevice Fabrication

In some embodiments, microchannels can be fabricated in the ECM membranes using conventional soft lithography. A prepolymer of polydimethylsiloxane) (PDMS) can be mixed with a curing agent at 10:1 (w/w) and degassed in a desiccator to remove air bubbles. The mixture can then casted on a photographically prepared silicon master and cured at 65° C. for at least 2 hours. After curing, the PDMS slab can be peeled off from the mold and cut into the desired size.

To construct multilayered microfluidic devices, upper and lower microchannels can be fabricated with a rectangular cross-section having the width and height of 500 μm and 100 μm, respectively. A 1 mm biopsy punch can be used to create fluidic access ports in these channels. To assemble a three-layer device, the lower channel slab can be gently dipped into a thin layer of uncured PDMS prepared by spin-coating of 10:3 PDMS on a Petri-dish at 2500 rpm for 5 minutes. When the slab is removed, the PDMS film can be transferred onto the surface containing the microchannel features as shown in FIG. 1F. Next, an ECM membrane can be placed over the lower channel on the PDMS-stamped surface, as shown in FIG. 1G, and cured at room temperature overnight. After curing, the upper channel slab can be coated with uncured PDMS using the same stamping technique and immediately bonded to the membrane-containing lower PDMS slab as shown in FIG. 1H. The assembled device can be left at room temperature overnight to ensure complete bonding.

Cell Culture

Human umbilical vein endothelial cells (HUVEC), both normal and GFP-expressing, can be cultured in EGM-2 medium. Murine pericytes genetically modified to express a tomato red color-labeled form of the pericyte marker Gli-1 and human lung adenocarcinoma cells (A549) can be cultured in standard 10% FBS containing DMEM medium. Human bronchial epithelial cells (BEAS-2b, ATCC) can be maintained in bronchial epithelial growth medium (BEGM). Normal human lung fibroblasts (NHLFs) can be cultured in FGM-2 medium.

Microfluidic Cell Culture

In some embodiments, microfluidic cell culture can be conducted in the three-layer microfluidic system described above. Prior to cell seeding, the microchannels can be incubated with the cell culture medium used for each cell type at 37° C. for at least 2 hours. For devices containing fibronectin-coated polyester membranes, 40 μgmL$^{-1}$ fibronectin solution can be introduced into the channels pretreated with corona point discharge and incubated at 37° C. and 5% CO2 for 30 minutes prior to incubation with cell culture medium. Next, cells suspended in culture medium at approximately 10 million cells per ml were injected into the upper channel (FIG. 10 and allowed to settle and attach to the membrane surface under static conditions at 37° C. and 5% CO2 for 2 hours. Following microscopic examination to confirm cell attachment, the microchannels can be gently flushed to remove non-adherent cells and then connected to syringe pumps that can generate a flow of culture medium at volumetric flow rates of 70-100 μlh$^{-1}$. Cells can be cultured for 24-72 hours with a continuous medium flow as needed to establish confluent mono-layers (as shown in FIG. 1J) and for over 7 days in select experiments. Cell viability can be assessed by fluorescence microscopy imaging of cells labeled with calcein-AM and ethidium bromide homodimer according to standard protocols (e.g., Live/Dead kit, Invitrogen, etc.).

Scanning Electronic Microscope (SEM) Results

In some embodiments, membrane samples for SEM can be fixed at 4° C. overnight in 2.5% glutaraldehyde and 2% paraformaldehyde in 0.1 M cacodylate buffer at pH 7.4. After several washing procedures, the membranes can be post-fixed in 2.0% osmium tetroxide for 1 hour, washed again in buffer, and dehydrated in a graded ethanol series. Subsequently, the samples can be taken through a graded hexamethyldisilazane (HMDS) series and air dried prior to mounting and sputter-coating with gold/palladium. SEM images of the membranes can be obtained using a scanning electron microscope. The obtained scanning electron micrographs can be analyzed using the Analyze Particles function of the ImageJ software to measure the size distribution of membrane pores.

AFM Nanoindentation

An atomic force microscope (AFM) can be used to characterize the mechanical properties of hydrated/wetted COL, COL-MAT and polyester membranes. A chromium-gold coated cantilever with a spring constant of 44.03 pN nm$^{-1}$ and a pyramid indenter can be used to obtain force-indentation curves. Young's modulus of the measured samples can be calculated from the force-indentation data using AtomicJ software.

Analysis of Membrane Permeability and Transparency

The optical transparency of ECM membranes can be quantified in the wavelength range of 350-700 nm using a standard spectrophotometer (i.e., Infinite M200, TECAN). To analyze permeability, ECM membrane-containing three-layer microfluidic devices can be created using the fabrication method detailed above. In this system, membrane permeability can be evaluated by loading the upper microchannel with a 20 kDa FITC-dextran solution (0.2 mM), collecting the outflow from the lower channel over 3 hours, and by measuring the fluorescence intensity of the collected samples using a fluorimetric plate reader (Infinite M200, TECAN). During these experiments, flows in the upper and lower channels can be driven in the same direction at 100 µl per hour for 3 hours. For comparison between different types of ECM membranes, data obtained from such measurements can be normalized to the average permeability of pure collagen (COL) membranes.

Analysis of Membrane Surface Adsorption

Absorption of biomolecules on membrane surfaces can be measured by treating bare COL membranes, pericyte-seeded COL membranes, and Transwell membranes with 1 mg ml$^{-1}$ fluorescein-conjugated bovine serum albumin (FITC-BSA) for 2 hours at 37° C. This can be followed by two washes with PBS for 5 minutes prior to detection and measurement of FITC fluorescence. The average fluorescence intensity from at least thirteen micrographs per group can be measured as the mean grey value using binarized images in the ImageJ software.

Immunofluorescence

After completion of cell culture experiments, the devices can be disconnected from the syringe pumps, and the channels can be washed gently 3 times by perfusing 1×PBS. Cells on the membrane surface can then be fixed by introducing 4% paraformaldehyde into both the upper and lower channels and incubating at room temperature for 15-20 minutes. The channels can then be washed three times with 1×PBS and stored in a humid, refrigerated environment prior to antibody labeling and fluorescence microscopy. Following cell permeabilization and blocking with 0.1% Triton-X and 3% bovine serum albumin (BSA) in 1×PBS for 30 minutes, the cells can be incubated with primary antibodies against FAK-Y397 (Cell Signaling), panlaminin and alpha-6 integrin diluted at 1:50 in 1% BSA containing 1×PBS solution for 2 hours at room temperature. Subsequently, the cells can be washed at least five times by gently flowing 1×PBS and then treated for 30-45 minutes with appropriate secondary antibodies diluted at 1:500 in 1×PBS containing 1% BSA. The actin cytoskeleton can be labeled using Alexa488-conjugated phalloidin at a concentration of 1 µgml$^{-1}$ in 1×PBS, either added alone or mixed with the secondary antibodies. Immunofluorescence imaging can be carried out using an inverted microscope with long working distance objectives. To quantify FAK activation on various membranes, ten randomly positioned high magnification fields per membrane type can be obtained. By using ImageJ software, at least 40 individual cells with clearly discernable borders can be selected as regions of interest to measure the averaged fluorescence intensity. Such data can be presented as the fluorescence intensity on a per cell basis, normalized to the signal obtained from cells cultured on untreated polyester Transwell membranes.

Statistical Analysis

Results can be reported as the mean±standard deviation. The statistical significance of variance across groups can be assessed by ANOVA with two-tailed Student's t-test for individual comparisons using GraphPad software.

Production of ECM-Derived Biomimetic Membranes

Figure 2B:
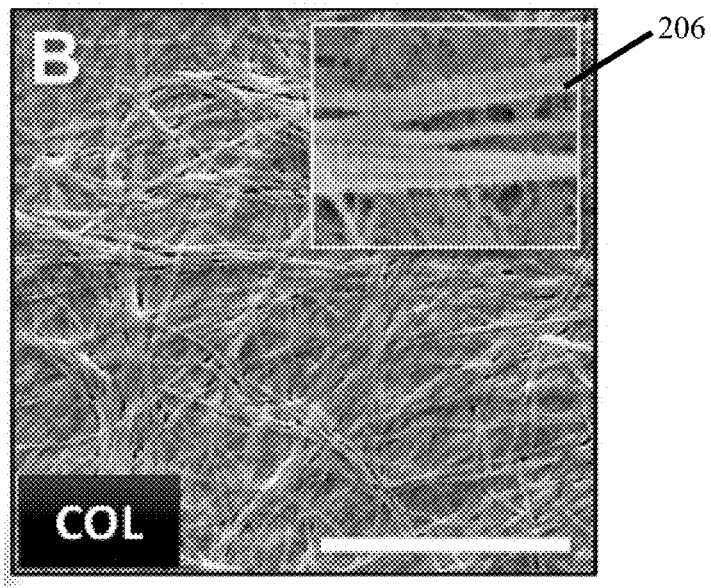

In some embodiments, the basement membrane can be composed of two structurally distinct layers. The first layer can be the basal lamina composed at least of cell adhesion molecules and anchoring filaments that adhere to the basolateral side of cells comprising epithelium, vascular endothelium, peripheral nerve axons, adipose tissue, and muscle. This ultrathin (i.e., <100 nm) layer can be connected to 3D networks of ECM fibers known as the reticular lamina. This specialized zone can serve to anchor the basal lamina to the underlying connective tissue and can serve to compartmentalize different tissue types. As the main ECM component of the reticular lamina, collagen can form striated fibrils that are assembled in a hierarchical manner to provide structural support to the basement membrane. Since collagen is a major structural protein, collagen type I can be used as a base material for developing a simple and cost-effective method to generate ECM-derived cell culture membranes. FIGS. 2A-2F are images illustrating the appearance, surface structure, and composition of the ECM-derived membranes. FIG. 2A illustrates a digital photo 210 of a COL-MAT membrane 110 held by forceps demonstrating mechanical integrity and transparency. As shown in FIG. 2A, the sequential process of collagen hydrogel dehydration can result in the formation of completely dried planar sheets within 48 hours that can be peeled, trimmed to desired dimensions, and easily handled using fine forceps. With 400 µl of collagen hydrogel uniformly spread over an area of 200 mm$^2$ (10 mm×20 mm), the average thickness of the resulting films can be measured to be 20 µm. The membrane thickness can be adjusted by changing the initial volume of collagen hydrogel and/or sequentially repeating the same rehydration cycle to deposit additional membrane layers.

FIG. 2B illustrates scanning electron microscopy (SEM) visualization of collagen type I (COL) membrane surface ultrastructure. The scale bar can equal 10 µm. Inset 206 illustrates characteristic banding pattern visible in larger fibrils. As shown by FIG. 2B, scanning electron microscopy results can reveal that the collagen (COL) membranes can consisted of randomly oriented fibrils organized into dense 3D networks mimicking the fibrous architecture of the basement membrane in vivo. The individual fibers comprising the meshwork can also exhibit the characteristic banding pattern of native fibrillar collagen (as shown in inset 206 of FIG. 2B). Furthermore, these membranes can include nanoscopic pores over the entire surface that are clearly visible in the scanning electron micrographs (as shown in inset 206 of FIG. 2B).

Based on these results, the feasibility can be analyzed of using the disclosed technique to create biomimetic membranes that mimic not only the structure of the basement membrane but also its ECM composition. The primary structural components of the basement membrane can be laminin and collagen type IV which can self-assemble into 3D networks with tissue-specific mixtures of proteoglycans and specialized glycoproteins such as entactin. To integrate these native constituents into the disclosed ECM membranes, composite hydrogels can be formed by mixing collagen with Matrigel, a reconstituted basement membrane-like material composed of approximately 60% laminin, 30% collagen IV, 8% entactin, proteoglycans, and various growth factors. Since Matrigel components do not covalently link to collagen type I during hydrogel polymerization, transglutaminase can be used after the rehydration (illustrated above with relation to FIG. 1C) to cross-link the Matrigel components with the polymerized collagen type I matrix.

Figure 2C:
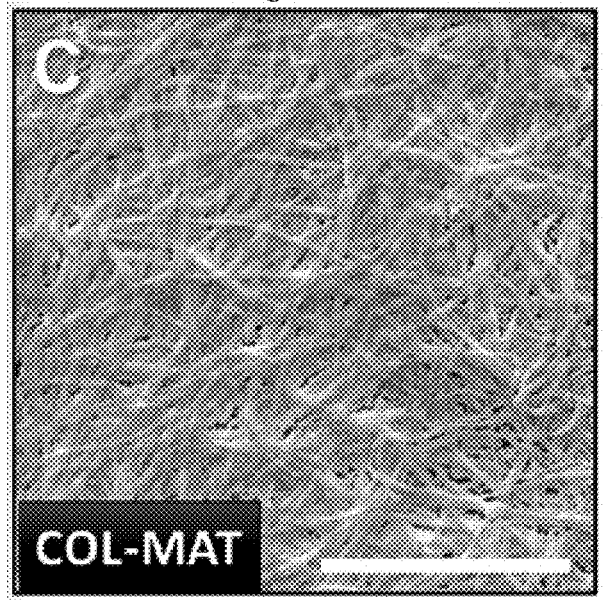
Figure 2D:
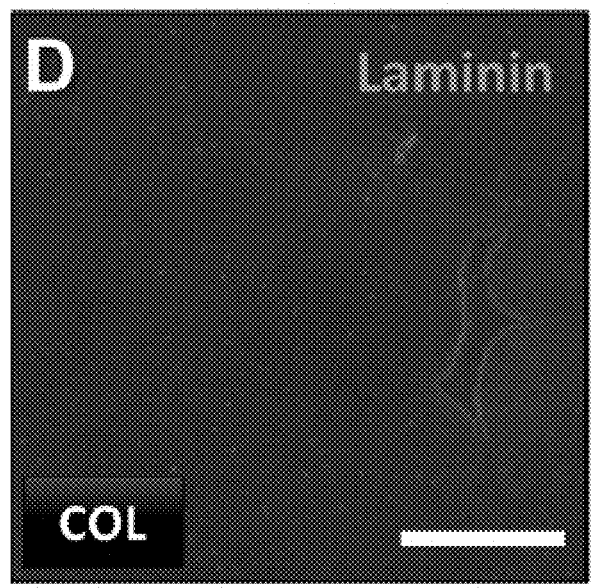
Figure 2E:
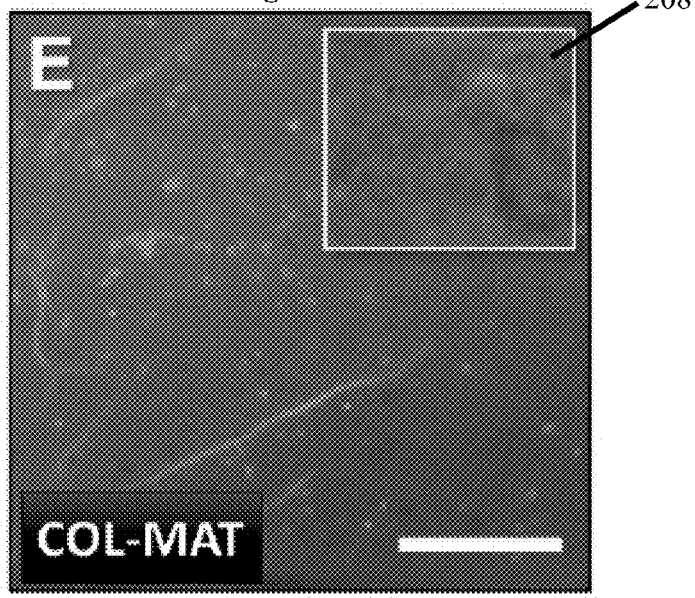
Figure 2F:
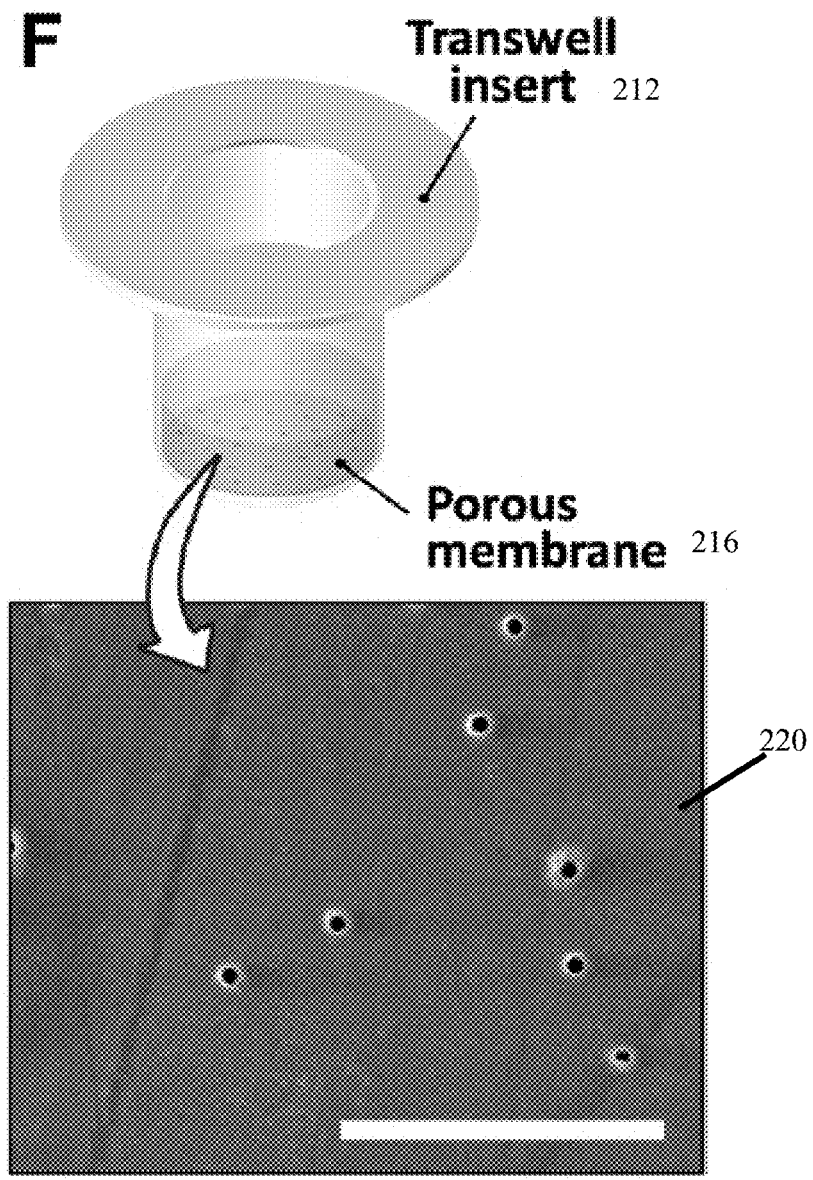

FIG. 2C illustrates SEM visualization of collagen type I and Matrigel composite (COL-MAT) membrane surface ultrastructure having a scale bar of 10 μm. As was the case with the COL membranes, the disclosed technique generated planar collagen-Matrigel (COL-MAT) membranes with similar thickness and structural integrity that consisted of densely packed ECM fibers (as shown in FIG. 2C). FIG. 2D illustrates immunofluorescence staining of laminin protein in COL membranes demonstrates an expected absence of laminin protein. The scale bar in FIG. 2D is 200 μm. FIG. 2E illustrates that immunofluorescence staining of laminin protein in COL-MAT membranes shows robust incorporation of laminin within the fibrous microarchitecture (as shown in inset 208 of FIG. 2E). The scale bar in FIG. 2E is 200 μm. Successful integration of Matrigel components can be evidenced by immunofluorescence detection of laminin in COL-MAT membranes. FIG. 2F illustrates the SEM visualization 220 of Transwell membrane surface ultrastructure having a Transwell insert 212 and showing 400 nm pores and smooth culture surfaces. The scale bar in SEM visualization 220 of FIG. 2F is 10 μm. The biomimetic structure and composition of the disclosed ECM membranes can be in stark contrast to the structure of commercially available Transwell cell culture membranes 216 that showed highly artificial and smooth surfaces with randomly distributed nanoscopic pores.

Taken together, these results illustrate the disclosed method allows for a technique to produce thin, porous membranes that closely approximate the structural organization and composition of the ECM in the native basement membrane.

Engineering the Properties of ECM Membranes

In some embodiments, the ability to vary the properties of cell culture membranes can facilitate engineering the insoluble cellular microenvironment that influences growth, differentiation, and maintenance of cells in an application-specific manner. Such capabilities can also be beneficial for modeling biomolecular transport and exchange of soluble factors between different tissue compartments. Moreover, the material characteristics of membrane inserts can become an important consideration for cell imaging and analysis commonly required for in vitro studies. By leveraging the flexibility to vary the type and composition of starting hydrogel materials, the disclosed fabrication technique can modulate at least the following properties of ECM membranes: optical transparency, permeability, and Young's modulus.

Optical Transparency

Figure 3A:
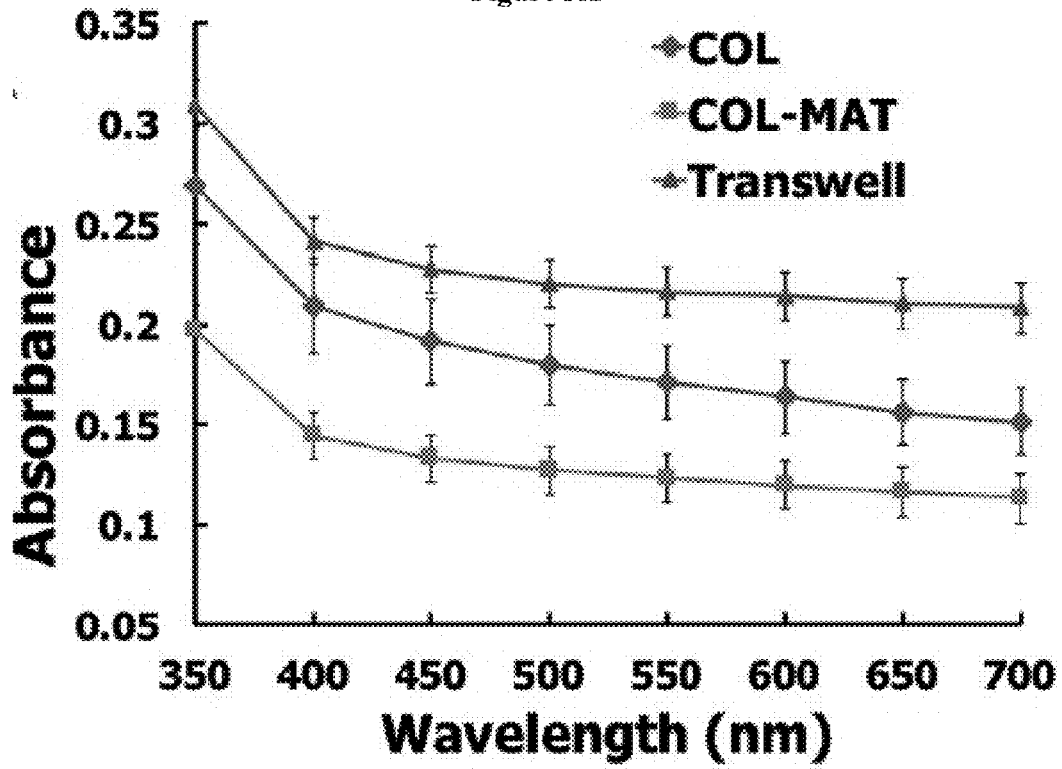
FIGS. 3A-3E illustrate experimental results illustrating the tunable biophysical properties of engineered ECM-derived membranes in accordance with an exemplary embodiment of the disclosed subject matter.
Figure 3B:
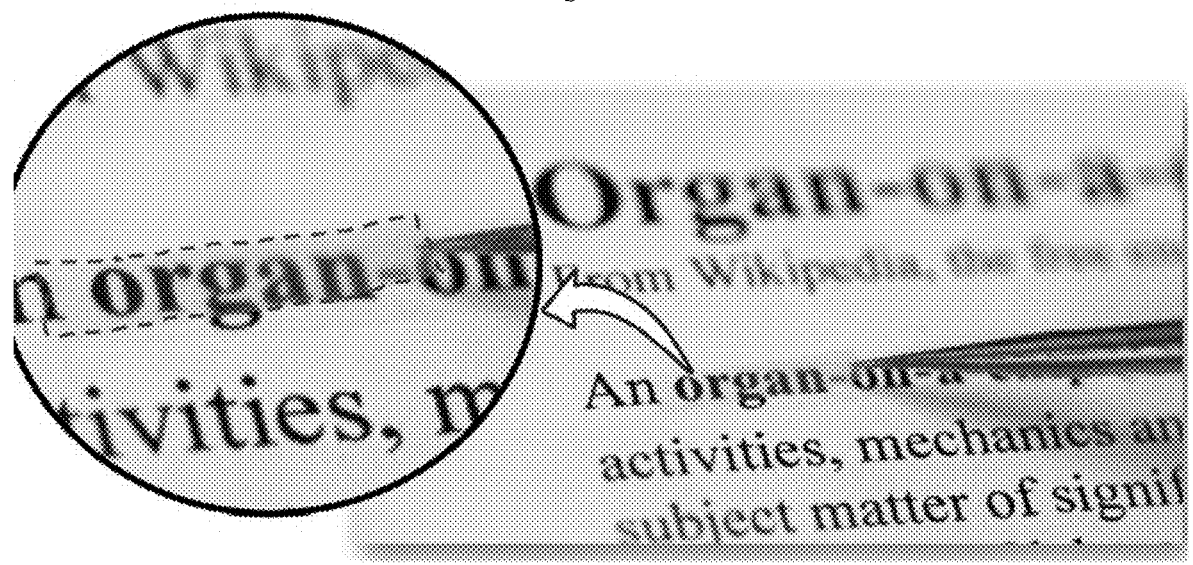

Optical transparency is an important property of membrane inserts desirable for microscopic imaging and analysis. In some embodiments, although ECM hydrogels can undergo dehydration and transformation during the fabrication procedure, their initial optical clarity can be retained relatively well, resulting in the formation of thin films whose transparency was superior to that of existing cell culture membranes. For example, FIG. 3A's analysis showed that the COL membranes absorbed less light across the visual spectrum compared to Transwell polyester (PE) membranes with 400 nm pores that are marketed as optically clear. FIG. 3A illustrates a plot of membrane absorbance from 350-700 nm. As shown in FIG. 3A, the ECM-derived membranes can exhibit superior optical transparency compared to traditional transparent cell culture inserts such as Transwell polyester membranes. When Matrigel is added to the collagen base, the resulting COL-MAT membranes can appear considerably more transparent to the naked eye (as illustrated in FIG. 3B). FIG. 3B illustrates a digital photograph of COL-MAT membrane demonstrating its optical clarity. This membrane can be trimmed to the approximate size used for device bonding and held over printed text using forceps. This observation can be supported by the spectrophotometric data that the light absorbance of the COL-MAT membranes was significantly lower than that of COL and clear Transwell PE membranes (as illustrated in FIG. 3A).

Permeability

In some embodiments, exchange of macromolecules, such as growth factors and cytokines, between adjacent tissue compartments can be essential for complex multicellular interactions that play a critical role in diverse physiological and patho-physiological processes. Biomolecular transport necessary for these types of interactions can require that the basement membrane be sufficiently permeable to large molecules. To find out whether the disclosed ECM membranes mimic this important feature of the native basement membrane, 20 kDa FITC-dextran can be used as a representative macromolecule and its transport across bare COL membranes embedded between two microfluidic channels can be measured under flow conditions.

Figure 3C:
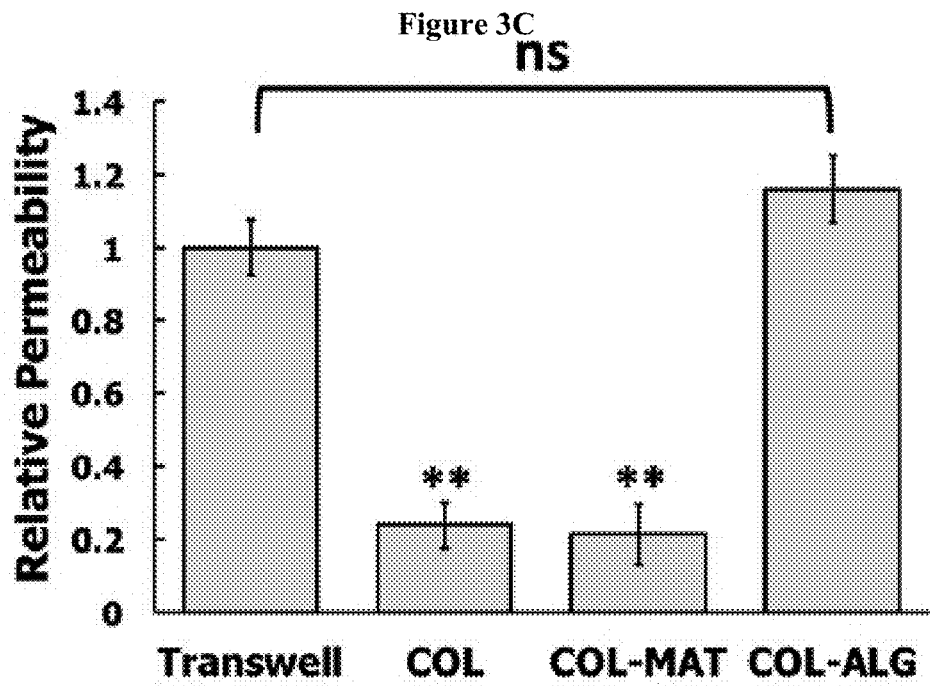

FIG. 3C illustrates a plot of relative membrane permeability representing measurements of 20 kDa FITC-dextran transport across COL, COL-MAT, COL-ALG, and PE membrane inserts over a period of 6 hours under continuous parallel flow perfusion at a flow rate of 100 μlh$^{-1}$. As shown in FIG. 3C, ** and ns represent P<0.01 and not significant, respectively. Fluorescence measurements of outflow collected from the microchannels can indicate that the COL membranes allowed translocation of dextran molecules due to externally imposed concentration gradients. Both COL and COL-MAT membranes, however, can be significantly less permeable than Transwell PE membranes with 400 nm pores (as illustrated by FIG. 3C), presumably due to their dense fiber architecture (as shown in FIG. 2B).

Figure 3D:
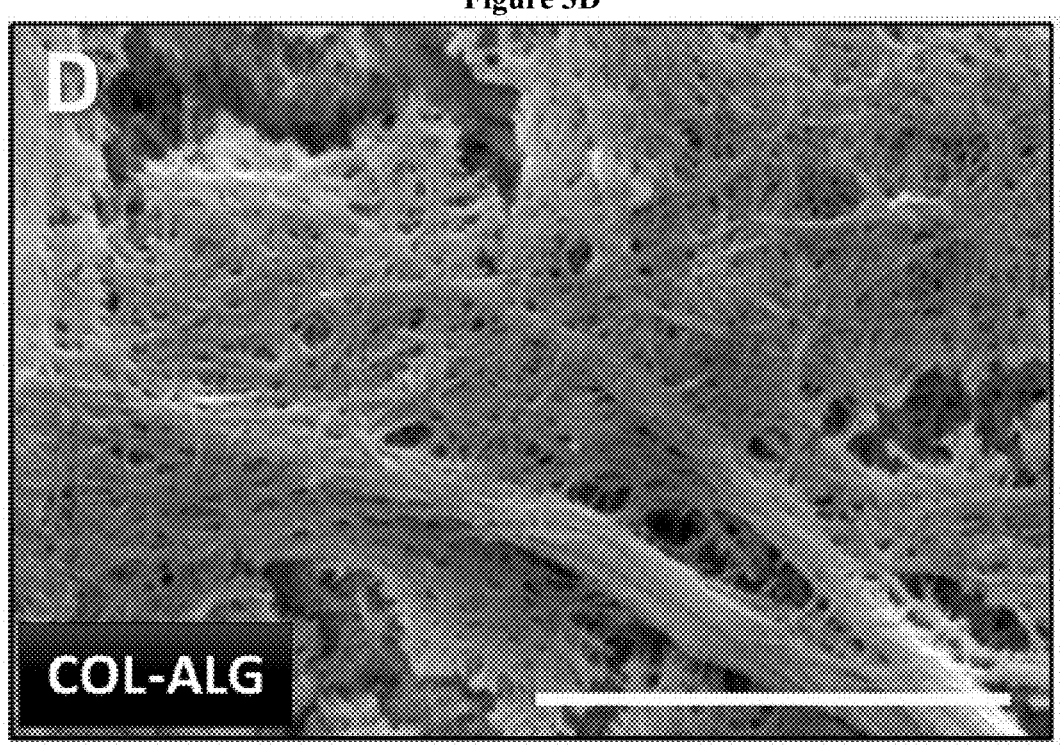

In some embodiments, to increase membrane permeability, another technique is provided in which water-soluble alginate (ALG) can be added to the collagen base and used as a sacrificial material that was dissolved away during the rehydration of initially dried films. FIG. 3D illustrates SEM visualization of collagen type I-alginate (COL-ALG) membrane surface ultrastructure demonstrating larger pores and fenestrations created by using alginate as a water-soluble sacrificial material. The scale bar of FIG. 3D is 2 μm. FIG. 3D's SEM visualization can show markedly increased bundling of collagen fibrils and more clearly visible fenestrations throughout the surface, suggesting increased membrane porosity. Quantitative analyses of the scanning electron micrographs can confirm that the average size of membrane pores in the COL-ALG membranes (700 nm) can be significantly larger than that in the COL membranes (250 nm). Consistent with these microscopic findings, the permeability of the COL-ALG membranes to 20 kDa FITC-dextran can be measured to be higher than that of COL membranes and Transwell PE membranes by a factor of 8 and 1.2, respectively (as illustrated in FIG. 3C).

Another factor that can impact the permeability of the disclosed ECM membranes is adsorption of biological molecules on the membrane surface. The disclosed assay using FITC-BSA can show that surface adsorption on the COL membranes can be significantly greater than that on Transwell polyester membranes. Binding and sequestration of biological molecules can be a critical function of the native ECM that is often challenging to replicate using synthetic cell culture membranes. Therefore, this unique property can be exploited to further enhance the biological activity of our ECM membranes in a controllable fashion.

Young's Modulus Measurement

In some embodiments, the stiffness of the basement membrane can vary significantly depending on the mechanical microenvironment of associated tissues. During early embryonic development, for example, the basement membrane can be more elastic to accommodate rapid growth and expansion of developing organs, whereas it can become stiffer at later stages to provide mechanical stability. Aging and various types of diseases (e.g., diabetes) can often be accompanied by significant stiffening of the basement membrane and its adjacent tissue. Replicating these physiologically relevant mechanical alterations of the native basement membrane in vitro can entails the ability to adjust the stiffness of cell culture membranes in a predetermined manner. To demonstrate this capability, the matrix composition of the disclosed ECM membranes can be varied and their Young's moduli can be measured using nano-indentation AFM.

Figure 3E:
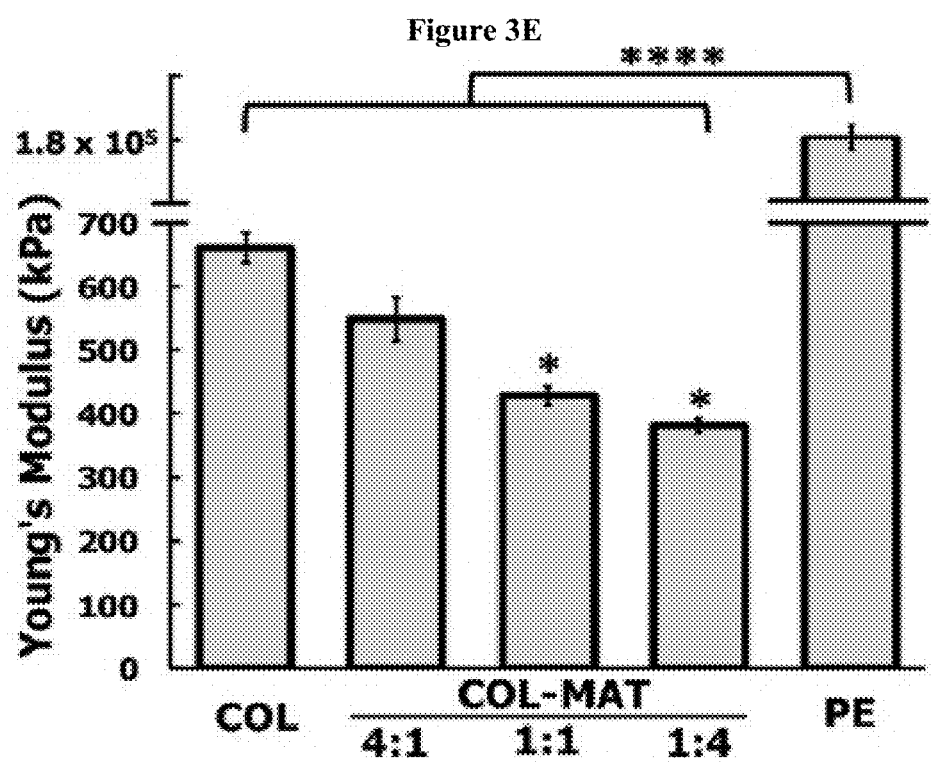

From qualitative visual examination, the dry ECM membranes prepared by the disclosed technique can be observed to be rigid and resistant to excessive bending and twisting, regardless of composition. When hydrated, however, the membranes can become softer and more compliant, exhibiting transition to a water-holding gelatinous appearance. FIG. 3E illustrates atomic force microscopy (AFM) nanoindentation measurement of the elastic modulus for hydrated COL, 80:20 COL-MAT, 50:50 COL-MAT, 20:80 COL-MAT, and Transwell PE membranes. As shown in FIG. 3E, * represents $P<0.05$. As plotted in FIG. 3E, the exemplary wetted COL membranes can have a mean Young's modulus of approximately 660 kPa. When collagen is blended with Matrigel at a volume ratio of 80:20 (collagen:Matrigel), the stiffness of the resultant COL-MAT membranes can decrease significantly, yielding a Young's modulus of 549 kPa. Increasing the volume fraction of Matrigel to 50% can lead to further reduction of Young's modulus down to 429 kPa. Since Matrigel is composed largely of globular basement membrane proteins, the observed changes in membrane stiffness can be likely due to the reduction in fibrous collagen type I, rendering the composite membranes more compliant. These results are comparable to the physiological ranges of basement membrane stiffness measured in several types of human tissue, including the lens capsule (0.3-2.4 MPa), retina (1 MPa), cochlea (37-135 kPa), and blood vessels (1-3 MPa). In contrast, hydrated Transwell PE membranes can be found to be more than 2 orders of magnitude stiffer, as demonstrated by their mean Young's modulus of 180 MPa (as illustrated in FIG. 3E). These data illustrate that the tunable stiffness of our ECM membranes and their potential as viable alternatives to conventional membrane inserts for modeling physiologically relevant biophysical microenvironments.

Incorporation of ECM Membranes into Microfluidic Culture

Figure 4:
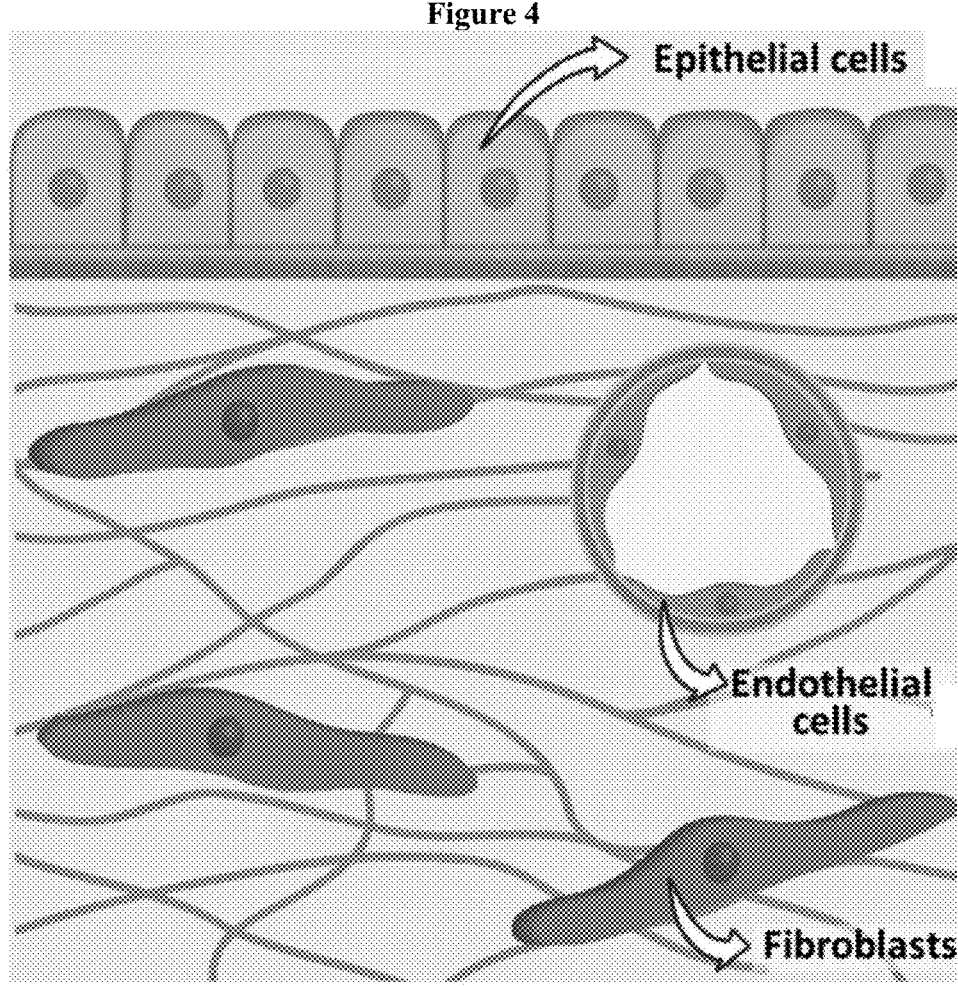
FIG. 4 is a diagram illustrating tissue architecture showing the different types of tissues of which the microfluidic analog components are depicted in FIGS. 5A-5G in accordance with an exemplary embodiment of the disclosed subject matter.

In some embodiments, the disclosed membranes can be used as cell culture substrates in microfluidic systems. FIG. 4 is a diagram illustrating tissue architecture showing the different types of tissues of which the microfluidic analog components are depicted in FIGS. 5A-5G. Epithelial cells shown in FIG. 4 are illustrated in greater detail in FIGS. 5C and 5D. The endothelial cells of FIG. 4 are illustrated in greater detail in FIG. 5E and fibroblasts of FIG. 4 are illustrated in greater detail in FIG. 5F.

Figure 5A:
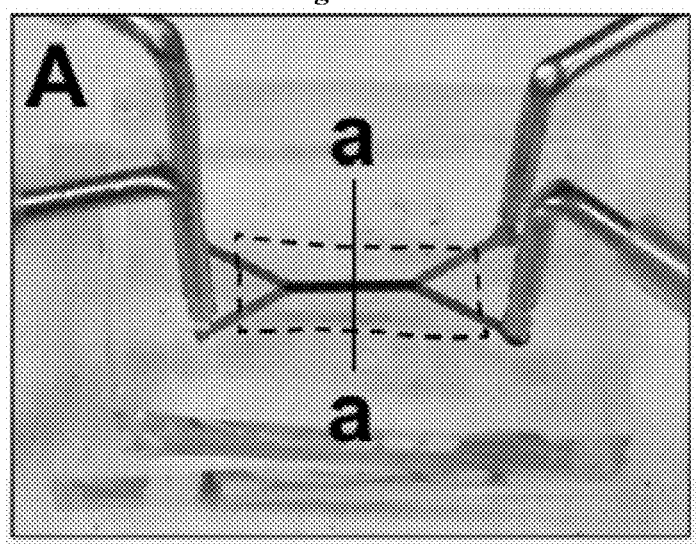
FIGS. 5A-5G are photographs and micrographs illustrating different aspects of the exemplary microfluidic cell cultures using ECM-derived membranes in accordance with an exemplary embodiment of the disclosed subject matter.

FIG. 5A illustrates a digital photograph of a microfluidic cell culture device composed of upper and lower microchannels separated by a COL-MAT membrane (shown with dotted lines). Injection of red and blue food coloring dyes demonstrates the patency of device bonding and partitioning function of the membrane. ECM membranes can be embedded between two parallel micro-channels to construct perfusable multilayer cell culture devices (as shown in FIG. 5A). The disclosed bonding technique based on adhesive layers of uncured PDMS (illustrated in FIG. 1F-H) can permit seamless integration of ECM membranes into the cell culture chambers without compromising structural integrity.

Figure 5B:
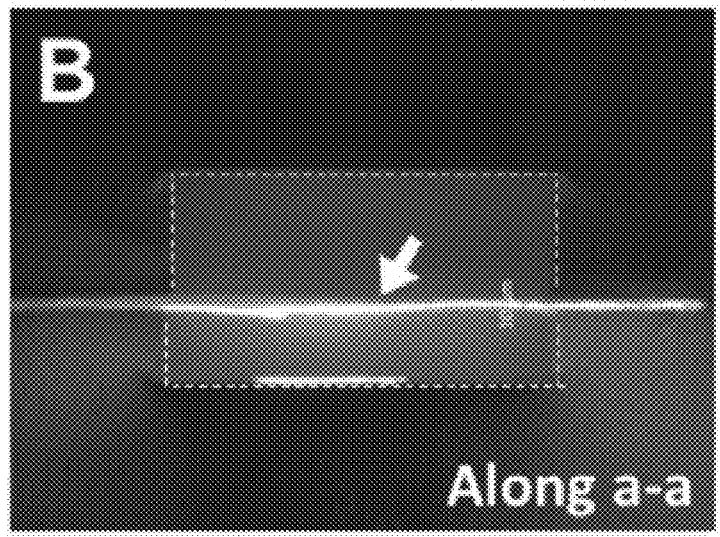

FIG. 5B illustrates a cross-sectional view of the device along line a-a shown in FIG. 5A. The ECM membrane indicated with a white arrow can be stained to visualize type I collagen. The dotted lines show the channel walls. The channel width can be 500 microns. Despite their small thickness, the membranes can remain intact and flat across the channel width during and after assembly (as illustrated in FIG. 5B). Hydration of the membranes with culture media prior to cell seeding can result in enhanced optical clarity but without any undesirable structural changes.

Figure 5C:
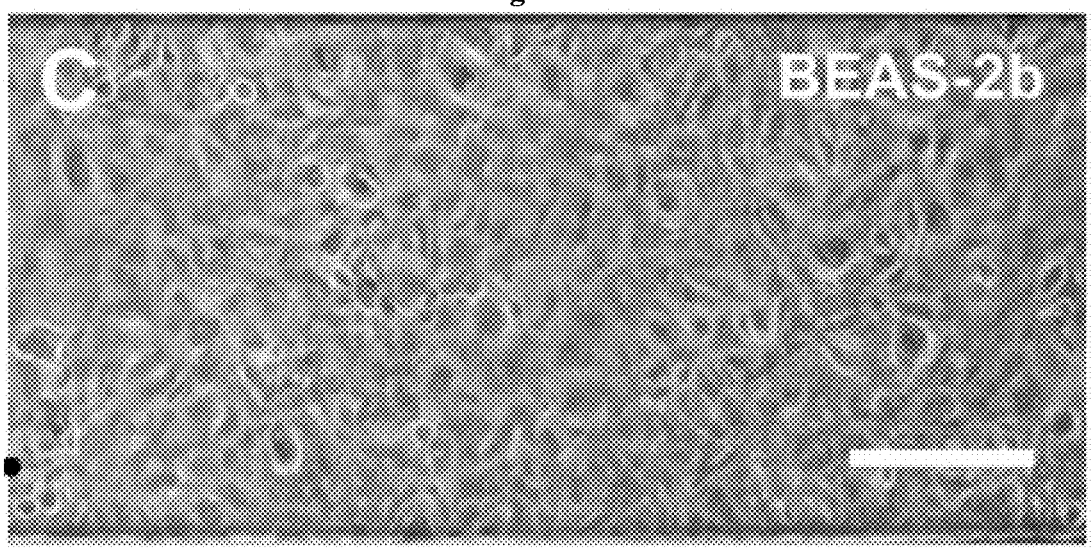
Figure 5D:
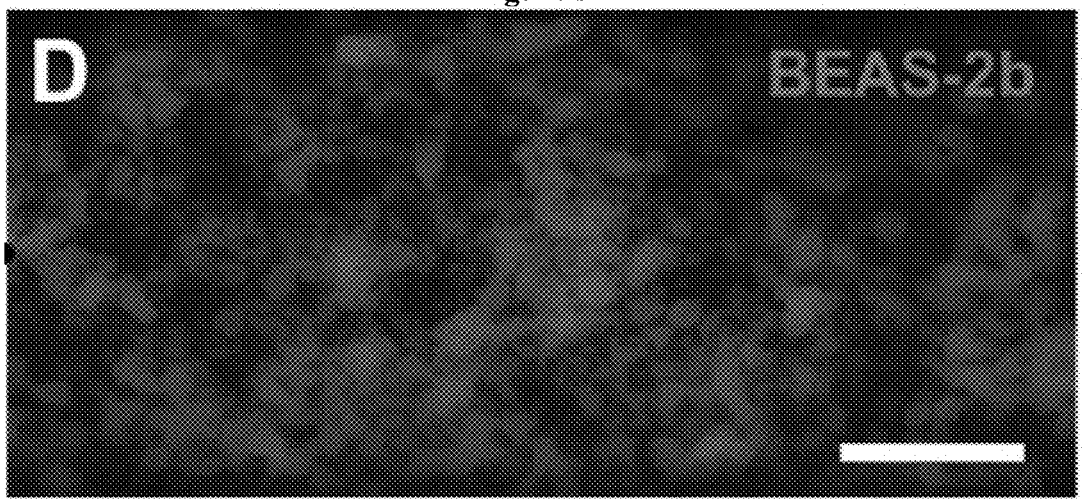

In some embodiments, to examine cell adhesion and growth on the disclosed ECM membranes, human bronchial epithelial cells (i.e., BEAS-2b) can be used as a representative cell population. When the cells are seeded into the disclosed devices containing COL membranes, they can attach to the membrane surface and can adhere within thirty minutes in the absence of flow. Cell adhesion in these devices could not require pre-treatment of channel surfaces with ECM solutions (e.g., a common technique for achieving cell attachment to synthetic substrates in conventional microfluidic systems). Under perfusion culture conditions, the cells can continue to proliferate over a period of 2-3 days until they form a confluent monolayer (as shown in FIGS. 5C and 5D). FIG. 5C illustrates a phase contrast micrograph of a confluent human bronchial epithelial cell (BEAS-2b) monolayer formed on a COL-membrane in a three-layer microdevice. The cells can be cultured for 72 hours under flow conditions at a flow rate of 100 $\mu l h^{-1}$. The scale bar of FIG. 5C is 200 µm. FIG. 5D illustrates a confluent monolayer of BEAS-2b cells stained with CellTracker dye. The scale bar of FIG. 5D is 200 µm.

Figure 5E:
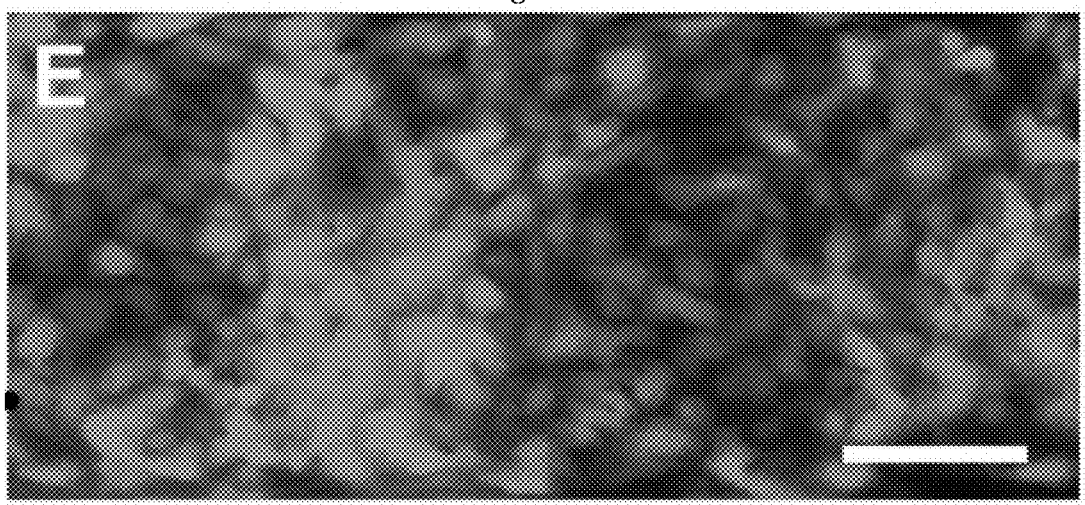
Figure 5F:
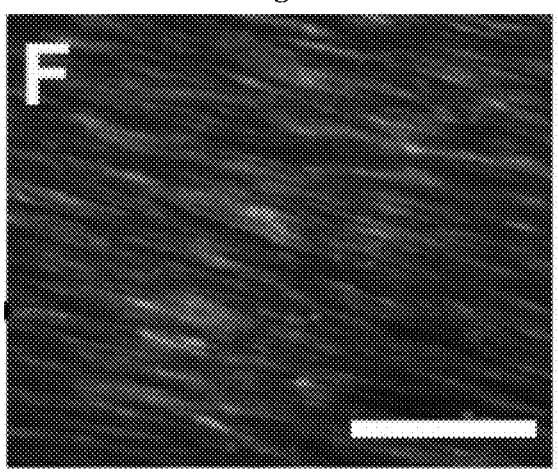
Figure 5G:
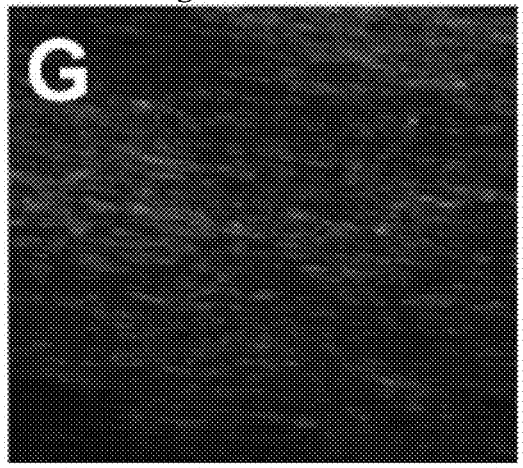

FIG. 5E illustrates human umbilical vein endothelial cells (HUVEC) grown to confluence on the surface of a COL-MAT membrane visualized by fluorescence imaging of constitutive fluorescent protein (GFP) expression following 48 hours of microfluidic perfusion culture at 100 µl hour. The scale bar of FIG. 5E is 200 µm. The same growth patterns can be observed in other cell types including endothelial (illustrated in FIG. 5E) and stromal cells seeded on the COL membranes (illustrated FIGS. 5F and 5G). FIG. 5G illustrates normal human lung fibroblasts (NHLFs) growing on the COL-MAT membrane surface. CellTracker dye can be used to visualize the cells. FIG. 5G illustrates immunofluorescence staining of alpha smooth muscle actin (α-SMA) in NHLFs cultured in the microdevice. The scale bars of both FIGS. 5F and 5G are 100 µm.

Direct observation and visualization of the cultured cells can be greatly facilitated by the optical transparency of the ECM membranes (illustrated in FIGS. 5A and 5C). At typical flow rates used in these experiments (70-100 $\mu l h^{-1}$), media perfusion through the microchannels could not have any measurable adverse effects on membrane integrity. Under these perfusion culture conditions, the COL substrates can maintain their original membrane architecture for extended periods (e.g., over one week) without a loss of structural integrity, demonstrating the long-term stability of our COL membranes and their resistance to cell-mediated proteolytic degradation.

Effect of ECM Membranes on Cell Adhesion and Growth

Figure 6A:
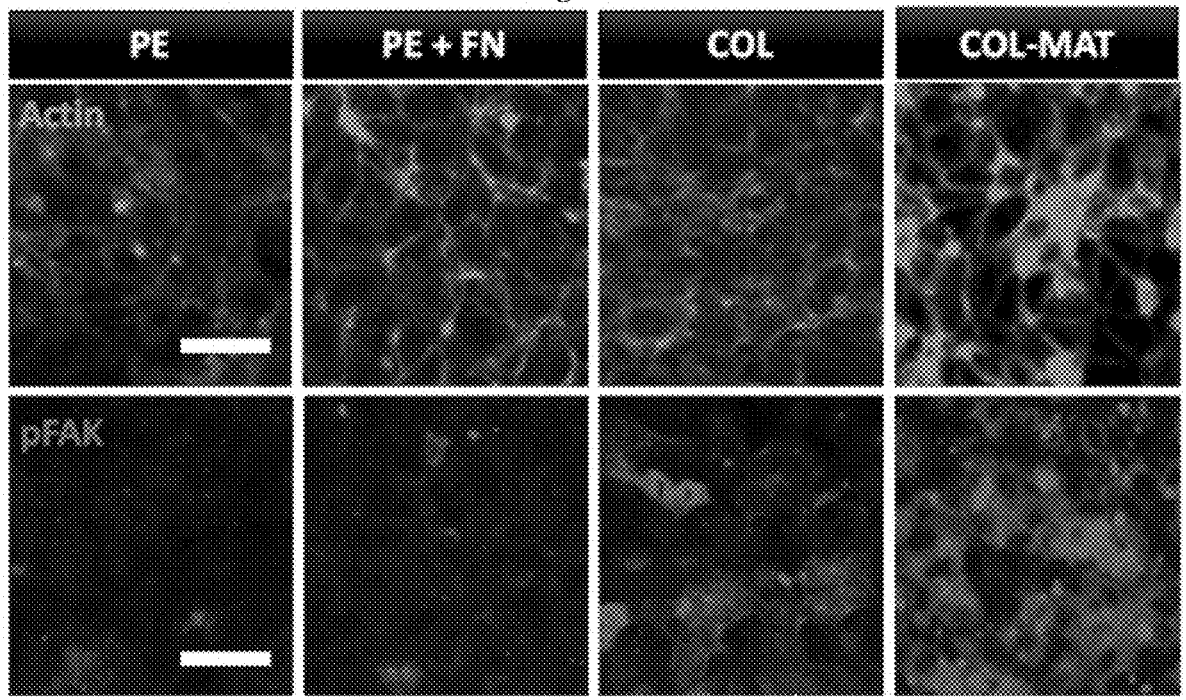
FIGS. 6A-6E depict measurement data and micrographs illustrating tunable cell adhesion and monolayer formation on engineered ECM membranes in accordance with an exemplary embodiment of the disclosed subject matter.

In some embodiments, after confirming the capacity of the disclosed membranes to support microfluidic cell culture, it was determined whether the ECM membranes offer significant advantages over traditional membrane inserts for promoting physiological cell-matrix interactions. To address this question, the phosphorylation of focal adhesion kinase (FAK) was quantitatively analyzed in monolayers of HUVECs cultured on different types of membrane substrates in the disclosed microfluidic device (as shown in FIG. 6A). FIG. 6A illustrates the impact of membrane composition on cytoskeletal organization (e.g., actin staining, top row of FIG. 6A) and focal adhesion-associated signaling (e.g., pFAK staining, bottom row of FIG. 6A) in cultured HUVECs. HUVECs can be seeded at high density and cultured for 6 hours on the surface of polyester (PE), fibronectin-coated polyester (PE+FN), COL, or COL-MAT membranes. Localized actin staining at cell borders can indicate rapid barrier organization following seeding on COL-MAT membranes. Staining of the phosphorylated form of focal adhesion kinase (pFAK) can localize adhesion-associated signaling complexes activated by adhesion to the respective membranes. Cells cultured on COL-MAT membranes can show significantly increased pFAK activities. The scale bar of FIG. 6A is 50 μm.

FAK can be an important component of the focal adhesion complex that undergoes phosphorylation in response to integrin engagement, and can serve as a key regulator of signaling pathways that mediate cell adhesion, proliferation, and a host of other critical cellular functions. In some embodiments, when the cells are grown on bare Transwell PE membranes sandwiched between two microchannels, they can show uniformly low levels of phosphorylated FAK (pFAK) throughout the monolayer. Incubation of the PE membranes with fibronectin solutions before cell seeding can lead to a slight increase in phosphorylation, presumably due to the absorption of fibronectin onto the membrane surface that facilitated cell adhesion and integrin-mediated signaling.

Figure 6B:
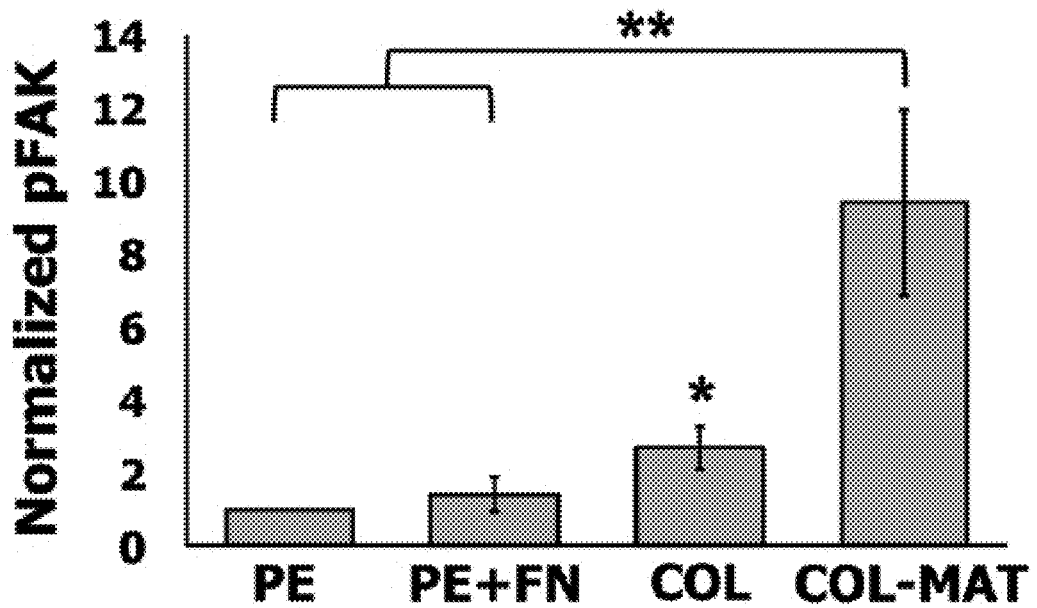

FIG. 6B illustrates quantification results of FAK phosphorylation on a per cell basis presented as the relative fluorescence intensity normalized to values obtained for uncoated PE membranes. As shown in FIG. 6B, * and ** show P<0.05 and P<0.01, respectively. When the COL membranes can be used in the disclosed device, however, pFAK staining can become significantly more pronounced as evidenced by a more than 2.5-fold increase in fluorescence intensity on a per cell basis (P<0.05)(as illustrated in FIG. 6B). This promotive effect can be further amplified by the incorporation of the COL-MAT membranes, in which case the levels of pFAK can be more than 9 times higher than those measured in the bare PE membranes (P<0.01) (illustrated in FIG. 6B). The increased FAK signaling on the composite membranes can also be accompanied by the assembly of actin stress fibers into thick bundles at the cell periphery, resulting in intense actin staining along cell-cell junctions. As demonstrated by these data, the disclosed membranes engineered from native ECM proteins can allow cells to engage the surface of their underlying substrates in a much more robust manner than is possible with certain synthetic membrane supports. Moreover, incorporation of basement membrane components into the disclosed membranes can provide an effective means to further increase integrin engagement and to induce cytoskeletal rearrangement that contributes to the formation of barrier tissue with enhanced structural integrity.

Figure 6C:
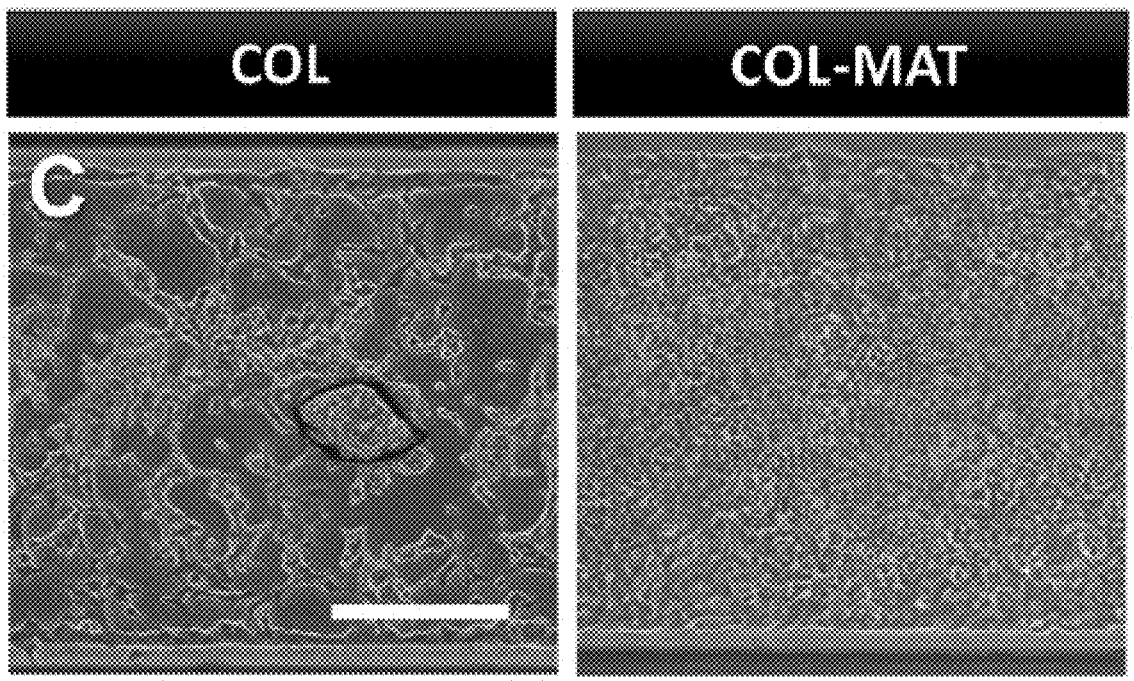

FIG. 6C illustrates phase contrast images of A549 cells growing as domed aggregates on COL membranes (left) or confluent monolayers on COL-MAT membranes (right). The cells can be cultured for 72 hours under continuous perfusion of culture media at 100 μl per hour. The scale bar of FIG. 6C is 200 μm. In some embodiments, differential cell adhesion responses observed in endothelial cells can also be found in other types of adherent cells. For example, human lung cancer cells (A549) cultured on the COL membranes in the disclosed device can exhibit an elongated morphology and 3D growth into dome-shaped aggregates, whereas they can form confluent 2D monolayers on the surface of COL-MAT membranes (as illustrated in FIG. 5C).

Figure 6D:
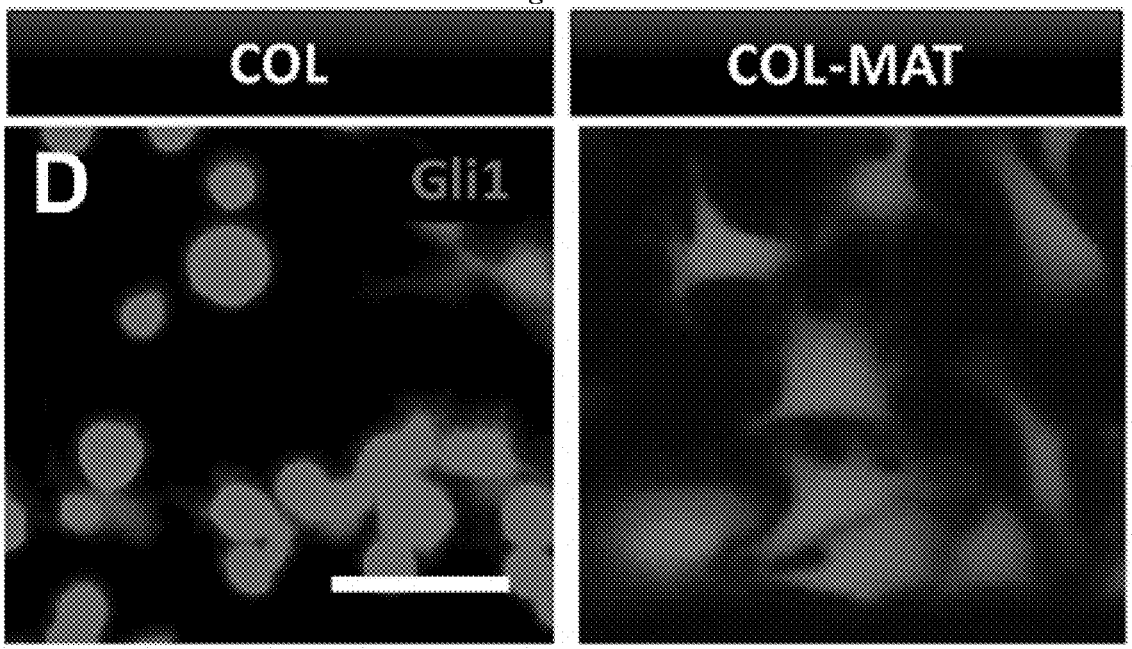
Figure 6E:
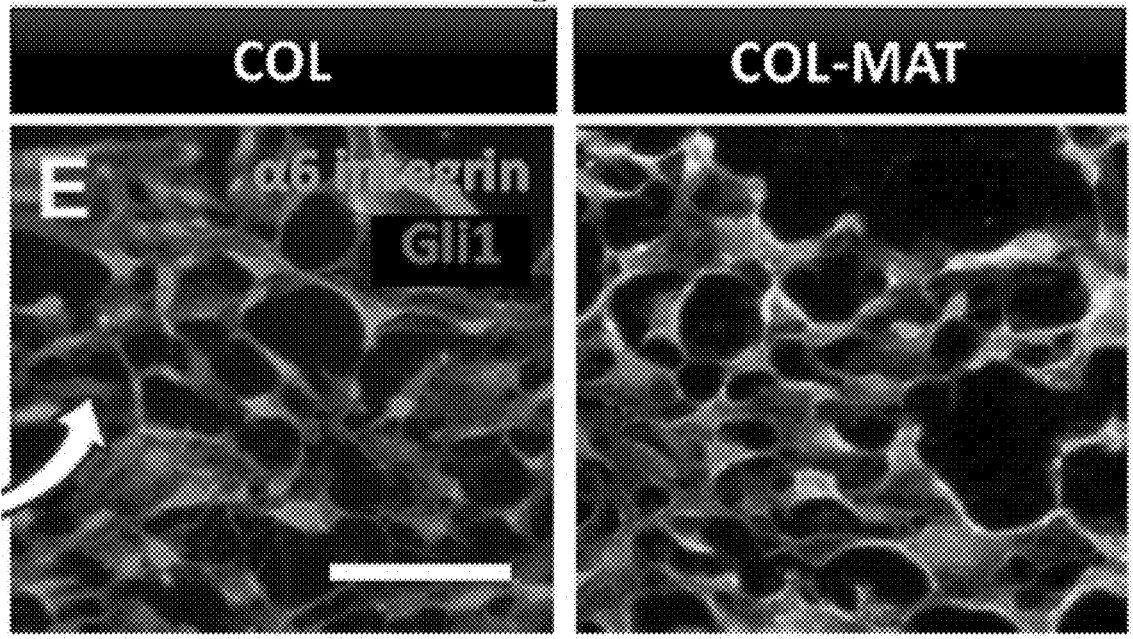

FIG. 6D illustrates pericytes spreading on COL (left) and COL-MAT (right) membranes in microfluidic channels. Pericytes can express a tomato red reporter of the Gli1 transcription factor. The scale bar of FIG. 6D is 100 μm. Pericytes, which can serve as a key cellular component of the endothelial basement membrane niche, can be another cell population that can show distinct responses to different membrane compositions. When these cells are seeded on the COL membranes, they can show poor adhesion and remained rounded without spreading by 4 hours post-seeding. In contrast, the COL-MAT membranes can allow the cells to rapidly attach, spread, and extend cellular projections within the same time (illustrated in FIG. 6D). The rapid pericyte adhesion and spreading observed on COL-MAT membranes can be due to the engagement of laminin-specific adhesion receptors such as the α6 integrin subunit. By allowing sufficient time for pericytes to adhere and spread on pure COL by 16 hours post-seeding, the α6 abundance and localization can be compared by immunofluorescence and observed markedly increased α6 staining on COL+MAT membranes (as shown in FIG. 6E). FIG. 6E illustrates alpha-6 integrin staining of pericytes (Gli1 reporter) following 16 hours of culture on COL (left) and COL-MAT (right) membranes. The scale bar of FIG. 6E is 200 μm. These simple examples can suggest the possibility of using the disclosed ECM membranes to control and rationally manipulate cell adhesion and growth in microfluidic cell culture models.

Construction of Microfluidic Tissue-Tissue Interfaces

In some embodiments, in microfluidic cell culture, semipermeable membrane inserts can be used predominantly as physical barriers that separate two or more adjacent cell culture chambers, while their porosity can allow for active and passive transport of fluids and various soluble factors between the chambers. This design can be commonly implemented in constructing compartmentalized cell culture models in which two distinct cell types can be cultured on either side of a porous membrane to replicate multicellular interfaces between two adjacent tissue compartments. In an exemplary embodiment, three-layer microfluidic devices can be created containing COL-MAT membranes as a platform to engineer various types of tissue-tissue interfaces without the requirement of any cell type-specific membrane coatings or other preprocessing.

Figure 7A:
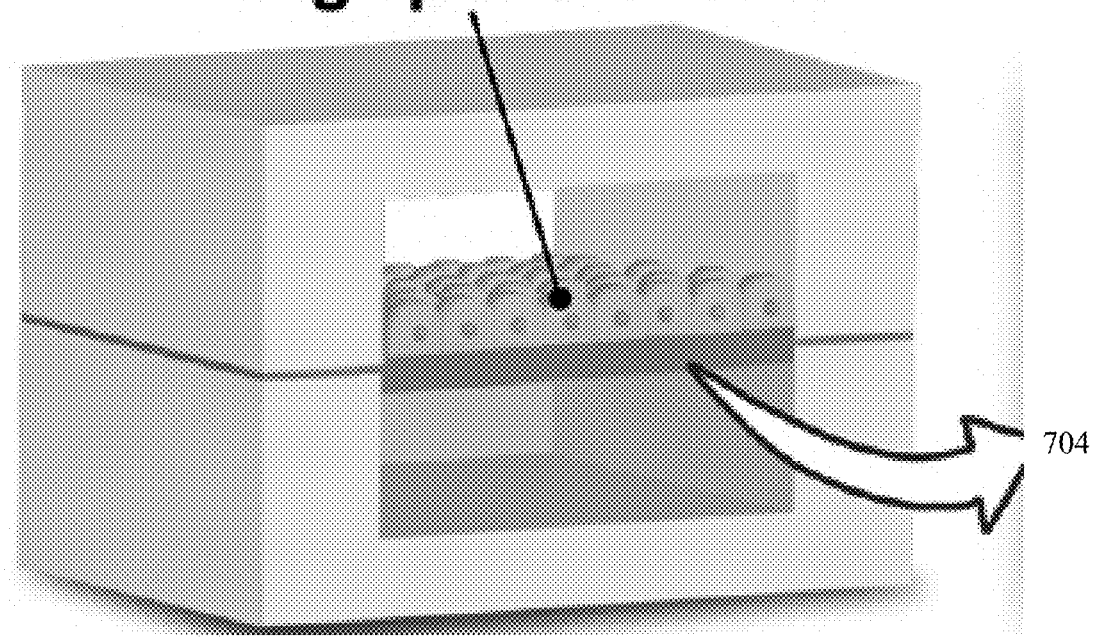
FIGS. 7A-7C are diagrams illustrating the air-liquid interface culture of human adenocarcinoma cells (A549) in an exemplary three-layer microfluidic device in accordance with an exemplary embodiment of the disclosed subject matter.
Figure 7B:
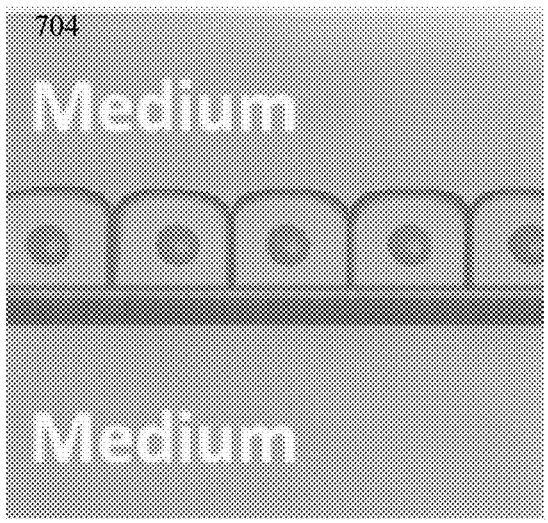
Figure 7C:
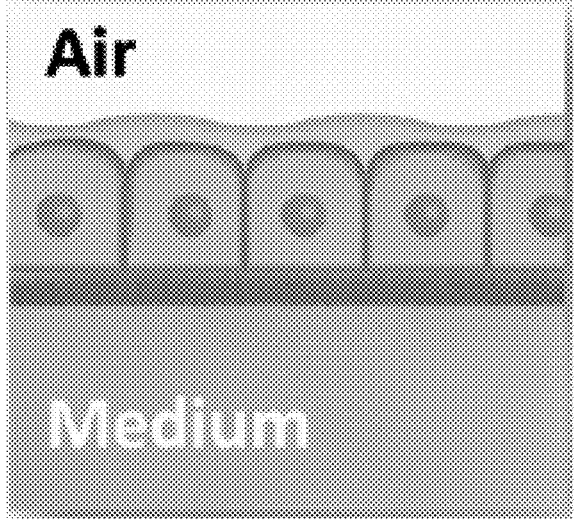
Figure 7D:
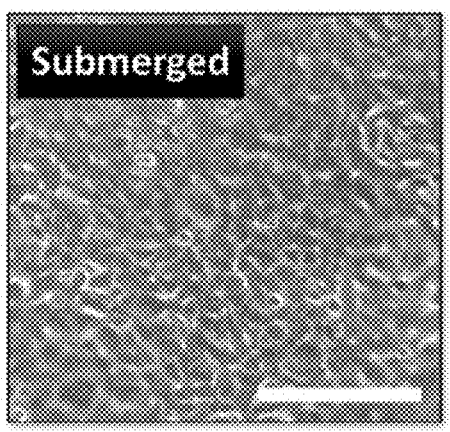
FIGS. 7D-7E are phase contrast images illustrating the confluent epithelial monolayers after 48 hours of submerged culture (FIG. 7D) and 72 hours of ALI culture (FIG. 7E) in accordance with an exemplary embodiment of the disclosed subject matter.
Figure 7E:
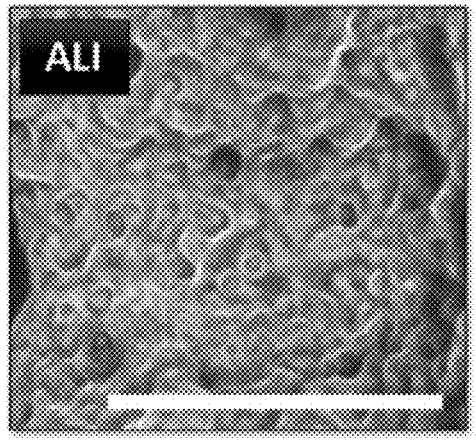
Figure 7F:
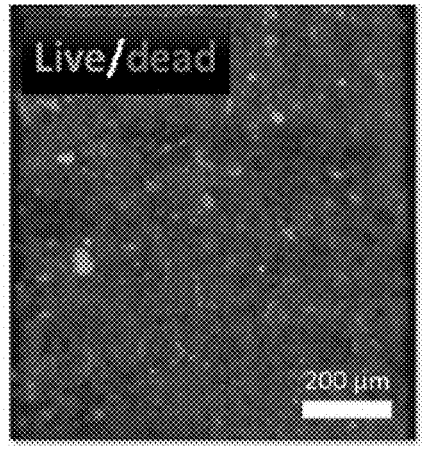
FIG. 7F is a fluorescence image illustrating the viability of cells cultured in the exemplary three-layer microfluidic device in accordance with an exemplary embodiment of the disclosed subject matter.

FIGS. 7A-7C are diagrams illustrating the air-liquid interface culture of human adenocarcinoma cells (A549) in a three-layer microfluidic device. FIG. 7B shows region 704 of FIG. 7A in greater detail. FIGS. 7D-7E are phase contrast images illustrating the confluent epithelial monolayers after 48 hours of submerged culture (FIG. 7D) and 72 hours of ALI culture (FIG. 7E). FIG. 7F is a fluorescence image illustrating the viability of cells cultured in the exemplary three-layer microfluidic device. The fluorescence image of FIG. 7F of the cells stained with calcein-AM fluorescence indicates virtually 100% viability. In some embodiments, microfluidic culture of human lung epithelial cells 702 can be implemented in the disclosed device to recreate the air-lung interface (as illustrated in FIGS. 7A-7C). To engineer this model, A549 lung cells can be cultured to confluence on the membrane surface of the upper chamber under continuous medium perfusion on both sides of the membrane. When the epithelial barrier has been formed, the medium can be gently aspirated from the upper chamber to expose the apical side of the cells to air. Owing to the permeability of our membranes, this configuration can permit basolateral feeding of the epithelial tissue, as illustrated by nearly 100% cell viability after 3 days of air-liquid interface (ALI) culture (as illustrated in FIG. 7E). The lung epithelial barrier in the disclosed system can remain viable for prolonged periods and effectively prevented leakage of culture medium from the lower chamber, allowing for stable maintenance of the micro-engineered air-lung interface. The scale bars of FIGS. 7D-7F are each 200 µm.

Figure 8A:
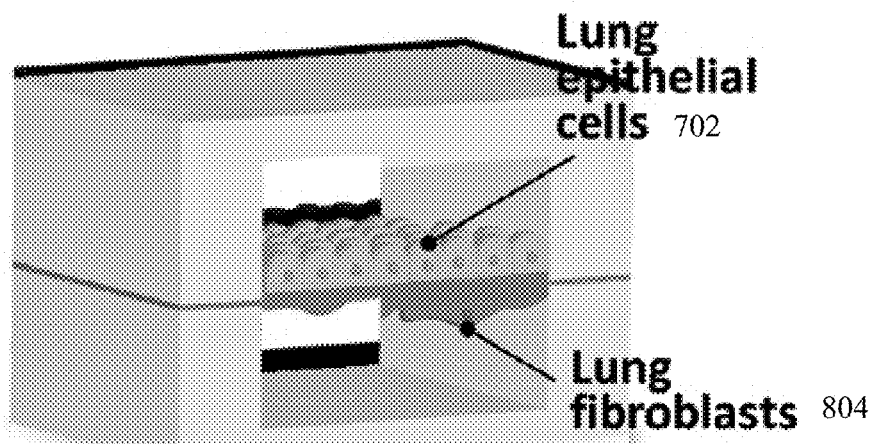
FIGS. 8A and 8B illustrate human bronchial epithelial cells that are cultured on the upper surface of an ECM membrane with human lung fibroblasts in accordance with an exemplary embodiment of the disclosed subject matter.
Figure 8B:
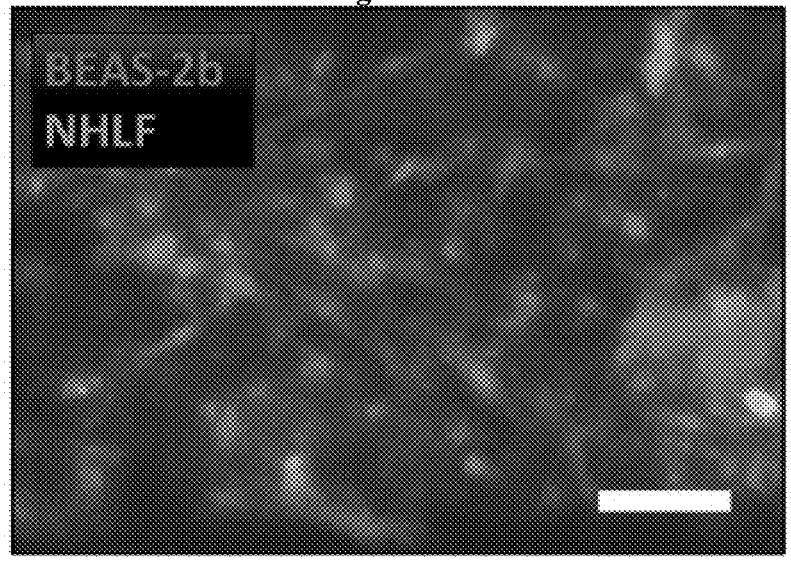
Figure 9A:
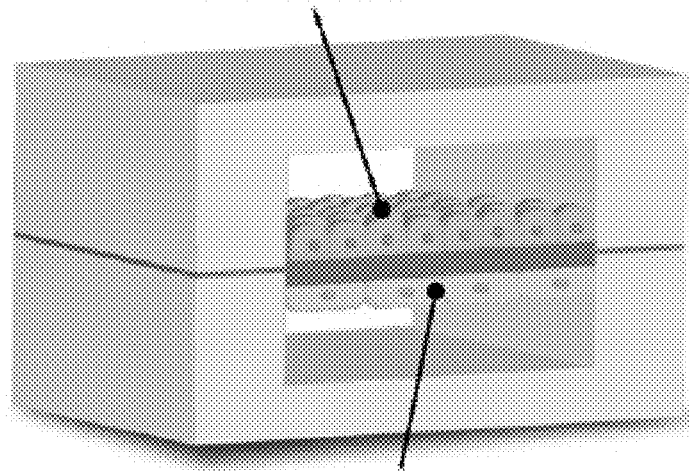
FIGS. 9A and 9B illustrate an exemplary epithelial-endothelial barrier composed of human bronchial epithelial cells and human venous endothelial cells in accordance with an exemplary embodiment of the disclosed subject matter.
Figure 9B:
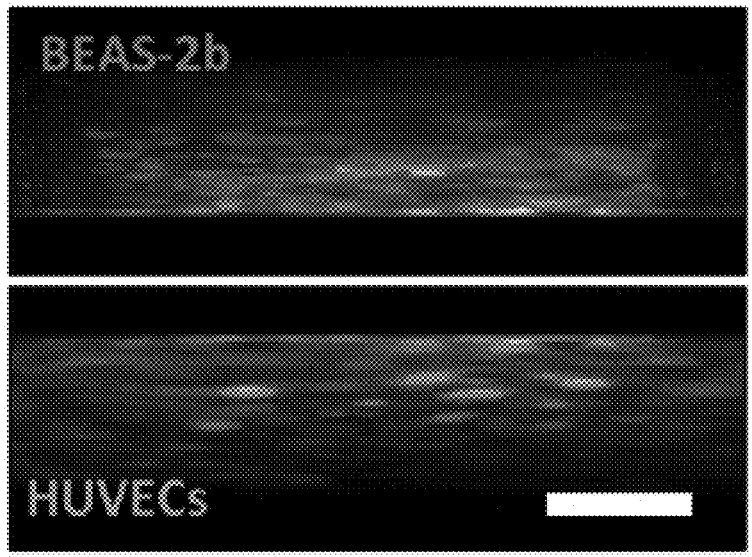
Figure 10A:
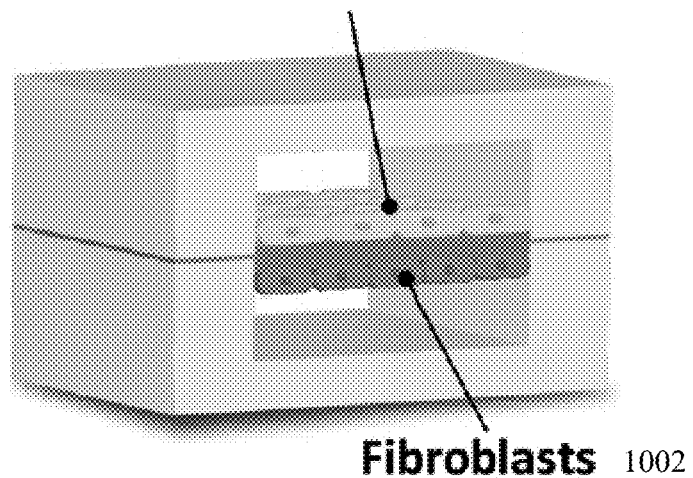
FIGS. 10A and 10B illustrate an exemplary co-culture of human umbilical vein endothelial cells (HUVECs) and human lung fibroblasts in accordance with an exemplary embodiment of the disclosed subject matter.
Figure 10B:
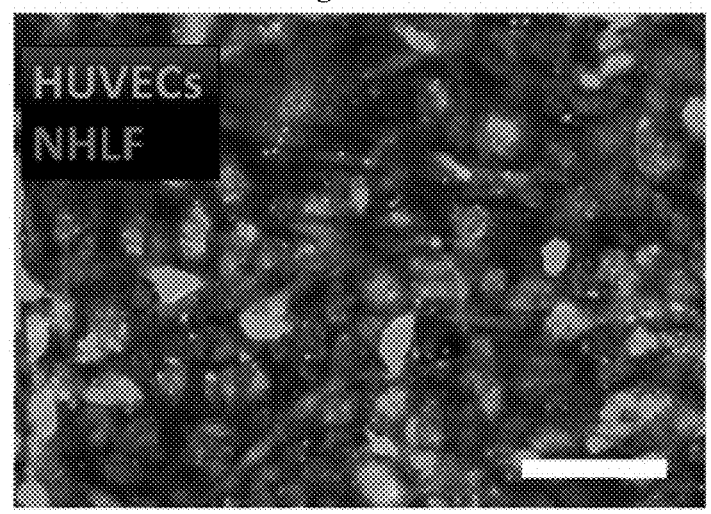

Building upon these results, co-culture models can be established and the structural organization of biological interfaces can be replicated between two different types of human tissue. Using the same 3-layer devices and perfusion culture techniques, for instance, living bilayer tissues reminiscent of the epithelial-stromal interface can be generated that include a monolayer of human bronchial epithelial cells 702 (BEAS-2b) and a layer of primary human lung fibroblasts 804 (NHLFs) separated by a COL-MAT membrane (illustrated in FIG. 8A). In this model, NHLFs were seeded at low densities and maintained in low-serum media to minimize cell proliferation and to mimic the loose cellularity of the sub-epithelial connective tissue in many organs. FIG. 8B illustrates human bronchial epithelial cells (BEAS-2b, CellTracker in FIG. 8B) that are cultured on the upper surface of an ECM membrane with human lung fibroblasts 804 (NHLFs, CellTracker in FIG. 8B) seeded at low density on the lower membrane surface to recreate the airway epithelial-stromal interface in the lung. The scale bar of FIG. 8B is 200 µm. Similar co-culture strategies were successfully applied to modeling the epithelial-endothelial (FIGS. 9A-9B) and vascular-stromal (FIG. 10A-10B) interfaces in our microfluidic system. FIGS. 9A and 9B illustrate epithelial 902-endothelial 904 barrier composed of human bronchial endothelial cells (BEAS-2b) cells (CellTracker in FIG. 9B) and human venous endothelial cells (HUVECs) (GFP, FIG. 9B) cultured on the opposite sides of a COL-MAT membrane. 3-D rendering can be conducted to show an angled view of the cell layers. The scale bar of FIG. 9B is 200 µm. FIGS. 10A and 10B illustrate co-culture of HUVECs 904 (FIG. 10B) and NHLFs 1002 (FIG. 10B). The scale bar of FIG. 10B is 200 µm.

Figure 11A:
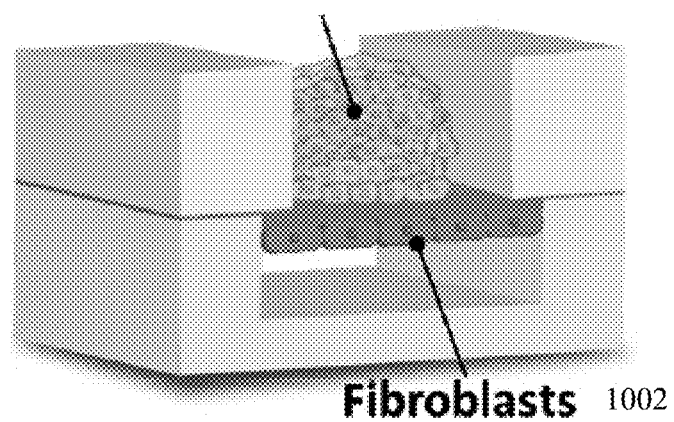
FIGS. 11A and 11B illustrate an exemplary preformed spheroid of human lung adeno-carcinoma cells that are grown on the upper membrane surface in a static PDMS microwell in accordance with an exemplary embodiment of the disclosed subject matter.
Figure 11B:
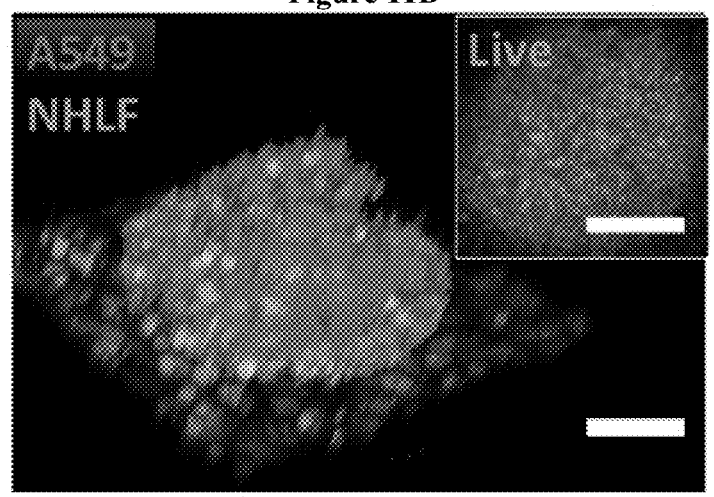

FIGS. 11A and 11B illustrate that a preformed spheroid of human lung adeno-carcinoma cells 1102 (A549, CellTracker) is grown on the upper membrane surface in a static PDMS microwell. NHLFs 1002 (FIG. 11B) are cultured on the other side of the membrane in a microfluidic channel to mimic the spatial arrangement of solid tumors and their associated stromal cells in the surrounding tissue. The scale bar of FIG. 11B is 200 µm. Confocal optical section of calcein-AM (FIG. 11B) staining in a representative spheroid cultured for 96 hours in the disclosed microdevice can demonstrate viability of cells throughout the spheroid. By modifying the design of the disclosed device to embed COL-MAT membranes between an open microwell and a bottom cell culture chamber, it is possible to explore the possibility of combining 3D spheroids with 2D tissue layers (illustrated in FIG. 11A). Tumor spheroids can be prepared by culturing A549 lung adenocarcinoma cells in agarose wells and can be introduced into the open well of our device. NHLFs can be seeded into the bottom chamber and grown on the other side of the membrane to model the architecture of solid tumors and their associated fibroblasts. Although adhesion of the spheroids to the membrane surface can induce outgrowth of cancer cells, the resultant spreading of the spheroids can be not significant enough to cause tissue disintegration, making it possible to retain the three-dimensionality and circularity of the spheroids, as shown in FIGS. 11A and 11B. The vast majority of the cells in the spheroids can remain viable throughout the culture period (as illustrated in FIG. 11B).

As demonstrated, the disclosed ECM membranes have the flexibility to accommodate co-culture of various cell types and provide stable structural scaffolds to reconstitute their relative spatial distributions in a physiologically relevant manner. These results can highlight the potential of the disclosed membranes as an essential building block of microfluidic co-culture systems to model various kinds of tissue-tissue interfaces during health and disease.

Fabrication of Organ/Tissue-Specific 3D Tissue Inserts by Combining ECM Materials and Living Cells In some embodiments, by extending the concept of engineering thin membrane inserts using ECM materials derived using the approaches described herein, mechanical compression-based approaches can be used for engineering thin 3D tissue constructs which may function as 'tissue inserts' in multilayer microfluidic assemblies.

The mechanical compression-based approach can be described as "squeeze water out of the gel to make it shrink". One unique aspect of these other techniques is that they can allow living cells to be embedded in the hydrogel and maintain their viability during the fabrication process. The geometry of the resultant tissue structures can also be engineered by patterning the initial hydrogel architecture, or by patterning the location of applied compression for a given architecture.

In some embodiments, a hydrogel matrix of choice (e.g., derived from ECM materials, d-ECM material derived from human tissues and organs, or hydrogels can be created using ECM materials derived from living cells and engineered tissues using the approaches described herein) can be loaded with living cells derived from the tissue type which the thin 3D tissue construct/insert is intended to mimic. In some embodiments, human fibroblasts can be utilized to create stromal tissue equivalents. The gel construct can be placed in a simple compression apparatus that utilizes externally applied weight or vacuum to rapidly remove liquid from the hydrogel, thereby increasing the density of matrix materials and cells and dramatically decreasing the thickness. Construct thickness can be precisely engineered by controlling the dimension to which the hydrogel can be compressed using spacers. After blotting away the removed liquid and releasing the construct from the compression apparatus, the resultant gel layers can be thin stromal tissue constructs that could function as thick, living tissue membranes in multilayer assemblies. These constructs can be durable and highly elastic, capable of being manually stretched without tearing or other mechanical damage, suggesting these constructs are ideal for use in multilayer microfluidic devices that incorporate mechanical stretch. The stromal cells inside the constructs show high viability following the compression process and the surface of the constructs is amenable to seeding with monolayers of other cells types, for example endothelial cells, as would be required for using these constructs as membrane-type layers in a multilayer organ-on-a-chip assembly.

Figure 12:
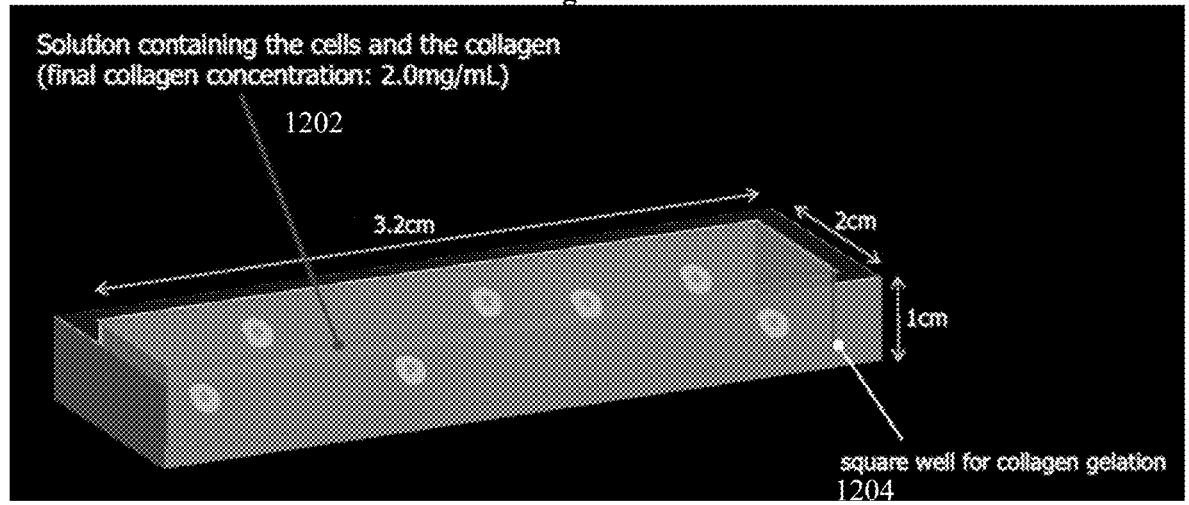
FIGS. 12 and 13 are diagrams illustrating the plastic compression of a fibroblast-laden collagen hydrogel to create thin 3-D stromal tissues for multilayer assemblies in accordance with an exemplary embodiment of the disclosed subject matter.
Figure 13:
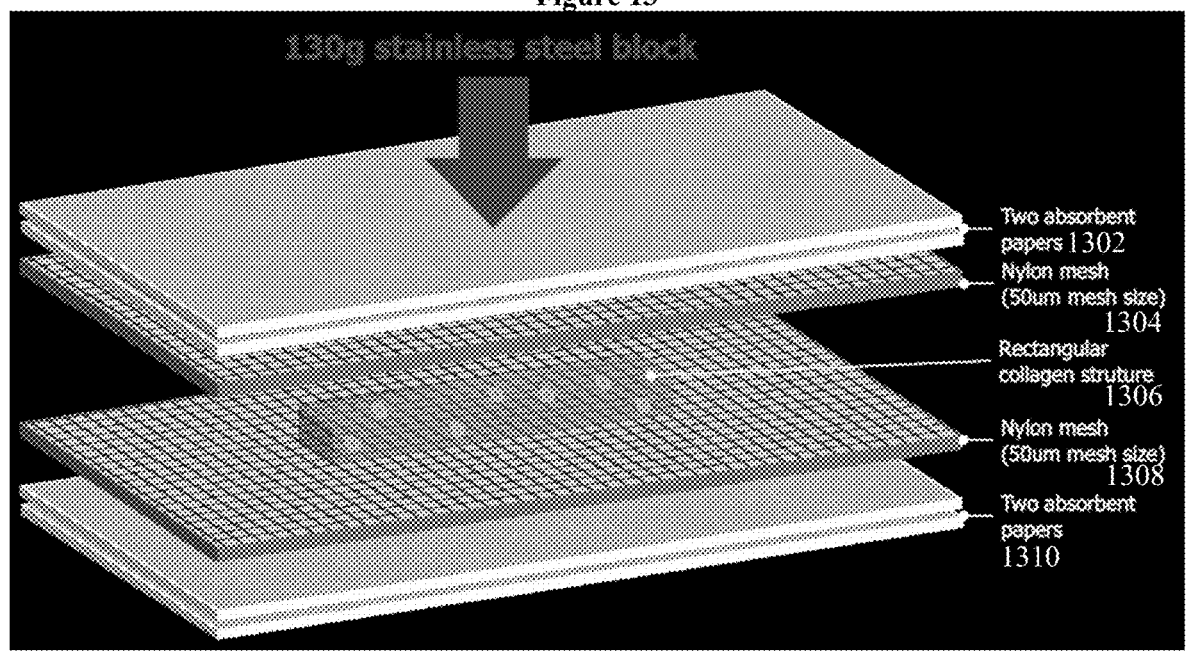

FIGS. 12 and 13 are diagrams illustrating the plastic compression of a fibroblast-laden collagen hydrogel to create thin three-dimensional stromal tissues for multilayer assemblies. FIGS. 12-13 illustrate hydrogel matrices that can be compacted by a combination of compression and blotting. In FIG. 12, solution 1202 can include cells and collagen (e.g., having a concentration of 2 mg/mL). The solution can be incubated for 30 minutes at 37° C. As illustrated in FIG. 13, the rectangular collagen structure 1306 shown in FIG. 15 can be compressed by placing a 130-gram stainless steel block. Two absorbent papers 1302, a nylon mesh 1304 can be placed between the collagen structure 1306 and stainless steel block. Additionally, two absorbent papers 1310 and a nylon mesh 1308 can be placed under the collagen structure 1306 when it is compressed using the stainless steel block.

Figure 14A:
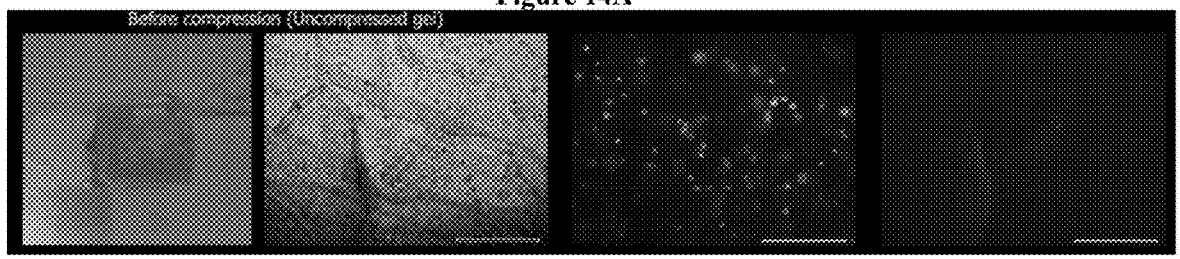
FIGS. 14A-14B are images that illustrate the gel before compression (FIG. 14A) and the gel after compression (FIG. 14B) in accordance with an exemplary embodiment of the disclosed subject matter.
Figure 14B:
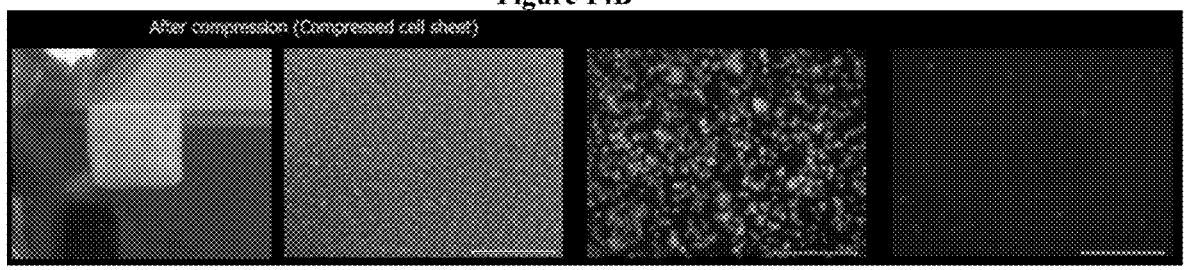

FIGS. 14A-14B are images that illustrate the gel before compression (FIG. 14A) and the gel after compression (FIG. 14B).

Figure 15A:
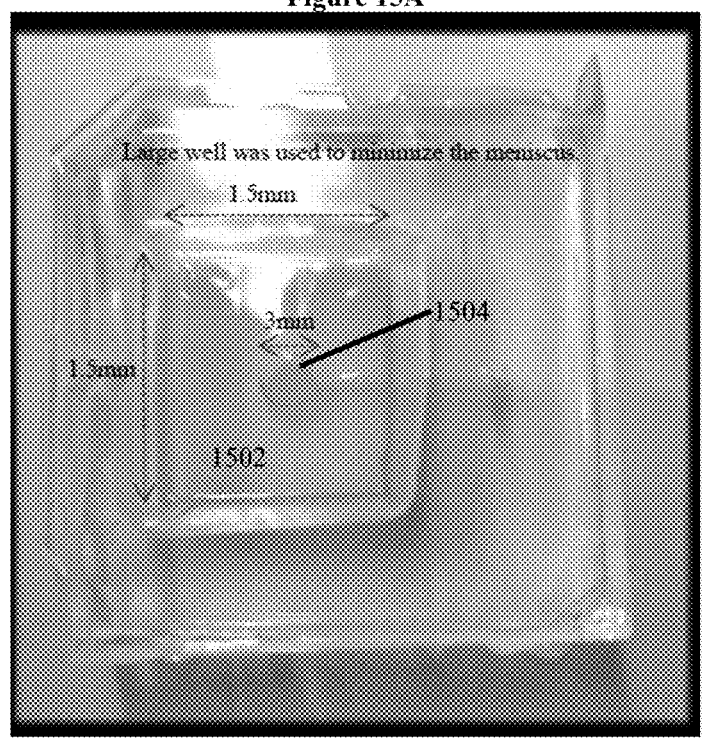
FIGS. 15A-15B are images that illustrate results of pneumatically compressed patterning of the ECM membrane gel in accordance with an exemplary embodiment of the disclosed subject matter.
Figure 15B:
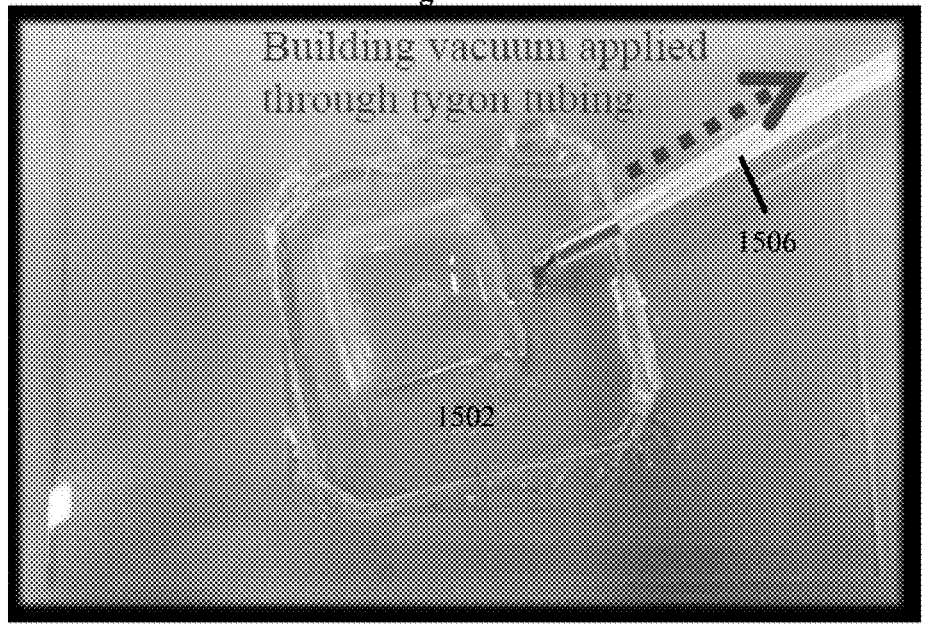

FIGS. 15A-15B are images that illustrate results of pneumatically compressed patterning of the ECM membrane gel. FIGS. 15A and 15B illustrate the feasibility of the pneumatically compressed patterning using a simple and easy to observe device. The membrane 1502 can be placed in a large well to minimize the meniscus during compression. The thickness of the gel 1504 at the center of the membrane can be less than 1 mm. The vacuum used for pneumatic compression can be created using Tygon tubing 1506 used to pressurize the well 1502.

Figure 16A:
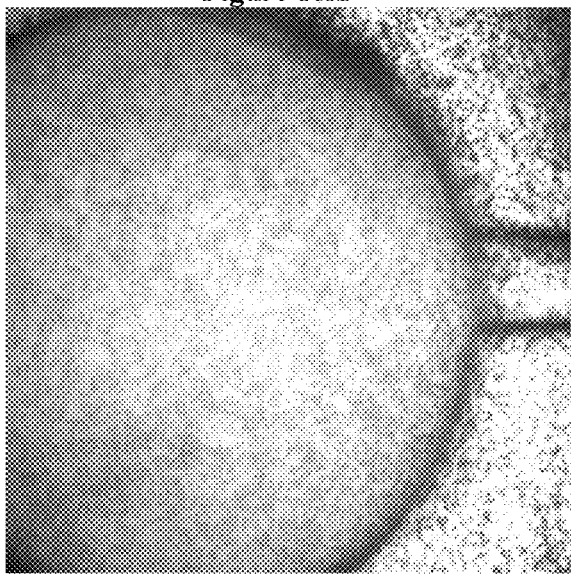
FIGS. 16A-16D are images that illustrate that the vacuum compressed area of the ECM membrane can be reduced in thickness upon being subjected to pneumatically compressed patterning in accordance with an exemplary embodiment of the disclosed subject matter.
Figure 16B:
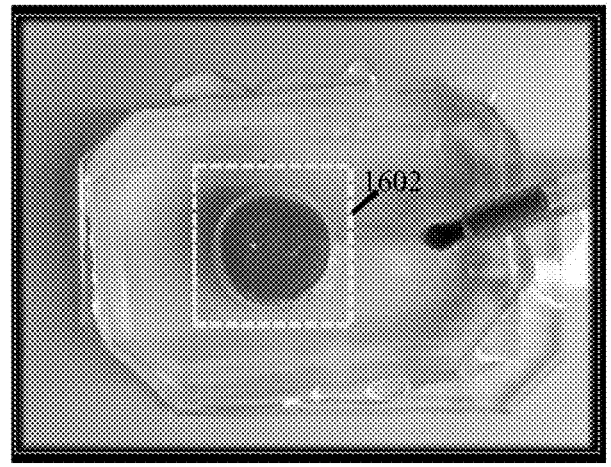
Figure 16C:
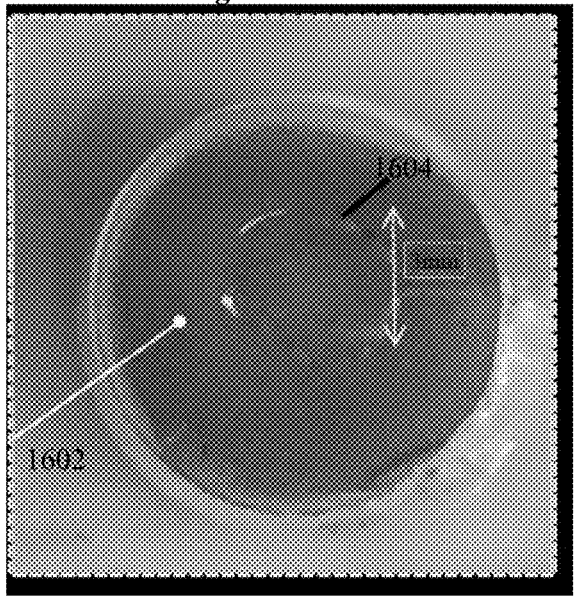
Figure 16D:
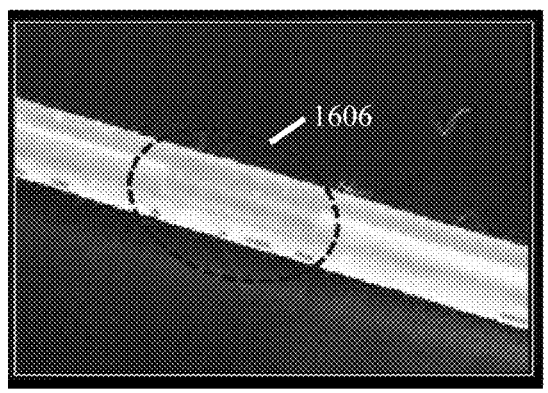

FIGS. 16A-16D are images that illustrate that the vacuum compressed area of the ECM membrane can be reduced in thickness upon being subjected to pneumatically compressed patterning. FIG. 16C illustrates region 1602 of FIG. 16B in greater detail. As illustrated in FIG. 16C, the vacuum compression region 1604 was reduced in thickness upon being subjected to pneumatically compressed patterning. After compression, liquid plugs 1606 can found in the Tygon tubing of FIG. 16D.

Figure 17A:
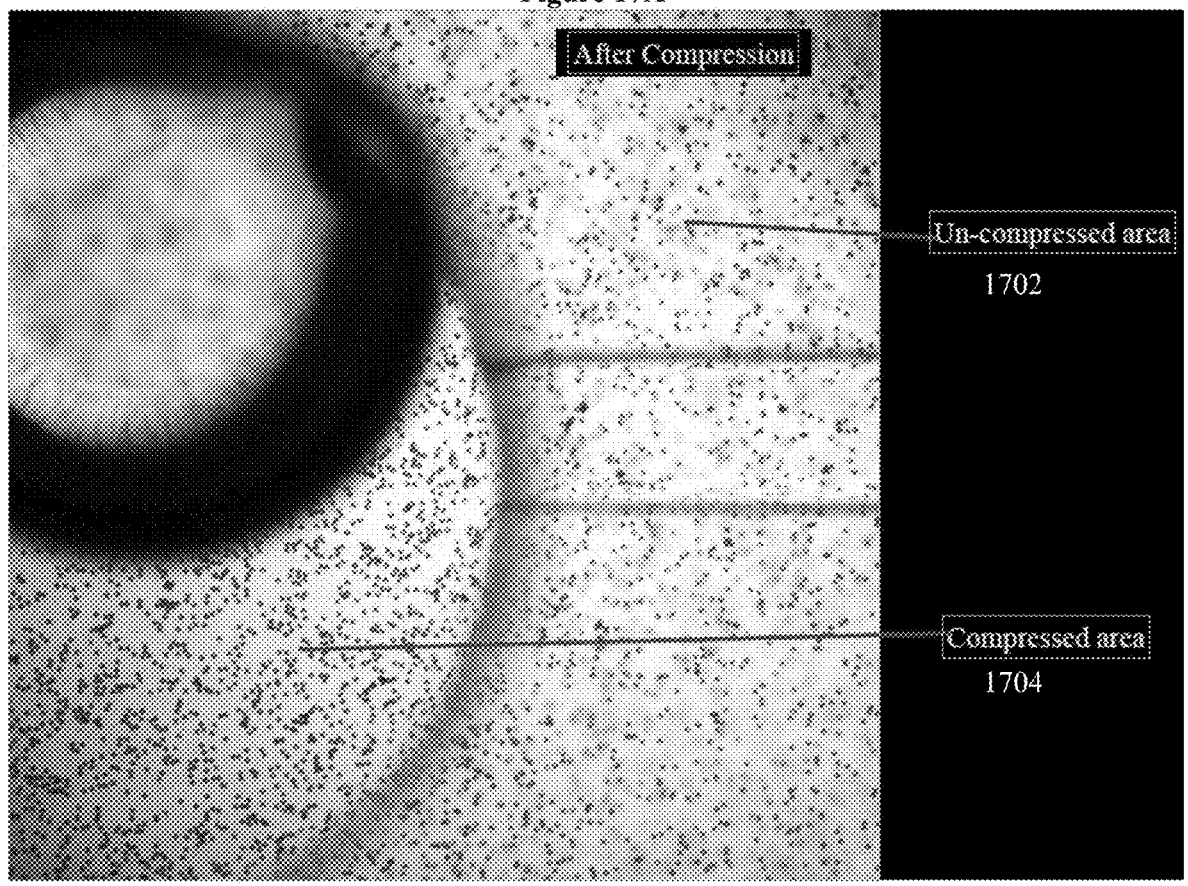
FIGS. 17A-17C are images that illustrate the compressed area and uncompressed areas of the ECM membrane upon being subjected to pneumatically compressed patterning in accordance with an exemplary embodiment of the disclosed subject matter.
Figure 17B:
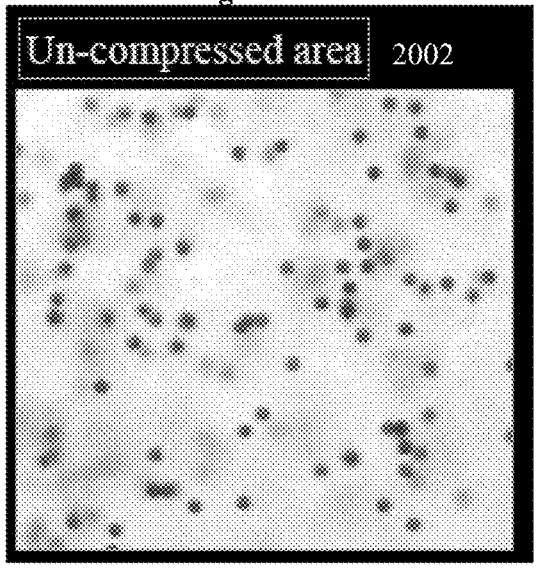
Figure 17C:
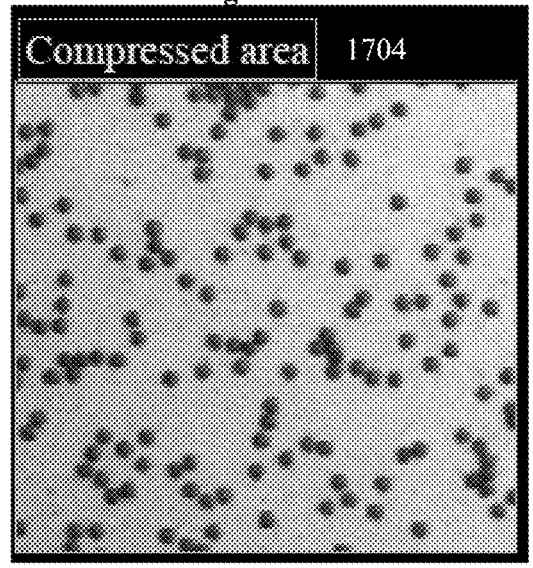

FIGS. 17A-17C are images that illustrate the compressed area and uncompressed areas of the ECM membrane upon being subjected to pneumatically compressed patterning. FIG. 17B illustrates the un-compressed area 1702 of FIG. 17A and FIG. 17C illustrates the compressed area 1702 of FIG. 17A.

In some embodiments, a modified plastic compression method can be used to perform compression for engineering thin 3D tissue constructs. In such a process, collagen type I hydrogel (2 mg/mL) can be loaded with human lung fibroblasts at a density of 1 million cells/ml is cultured for 24 hours in detached floating culture.

Figure 18:
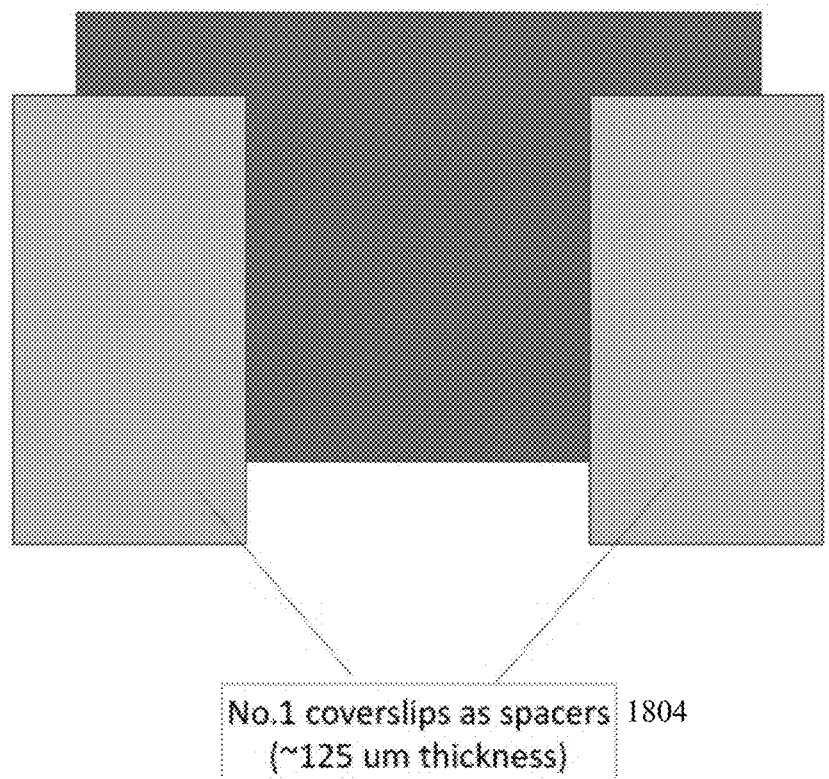
FIG. 18 is a diagram of an exemplary setup for performing plastic compression of a collagen hydrogel loaded with human lung fibroblasts in accordance with an exemplary embodiment of the disclosed subject matter.

FIG. 18 is a diagram of an exemplary setup for performing plastic compression of a collagen hydrogel loaded with human lung fibroblasts. The gel construct can be placed in a simple compression apparatus comprised of large microscope slides and coverslips that function as spacers (as illustrated in FIG. 18). Using either single or double layers of No. 1 coverslips 1804 with thickness of ~125 microns, gels can be compressed to estimated thicknesses of ~125 microns or ~250 microns, respectively.

Figure 19A:
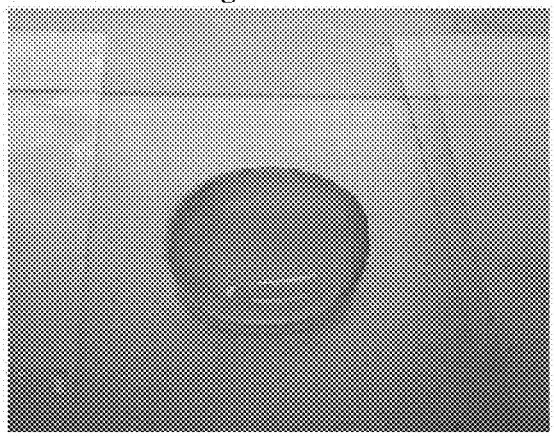
FIGS. 19A and 19B are diagrams of the collagen hydrogel loaded with human lung fibroblasts arranged in the exemplary setup for plastic compression in accordance with an exemplary embodiment of the disclosed subject matter.
Figure 19B:
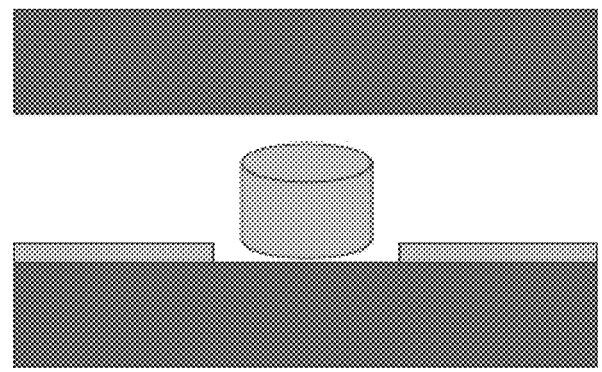
Figure 20A:
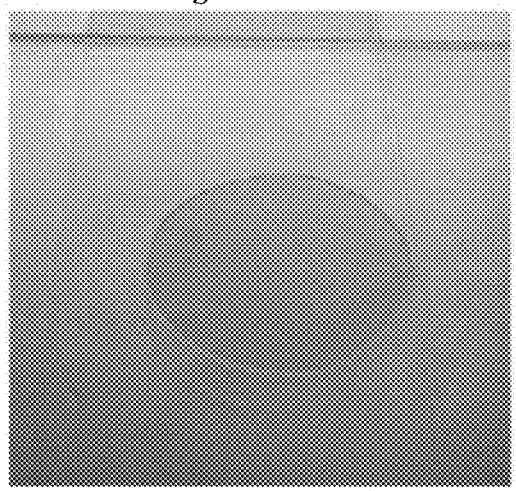
FIGS. 20A and 20B are diagrams of the plastic compression being performed on the collagen hydrogel loaded with human lung fibroblasts in accordance with an exemplary embodiment of the disclosed subject matter.
Figure 20B:
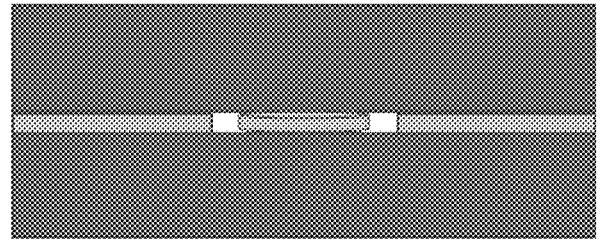
Figure 21:
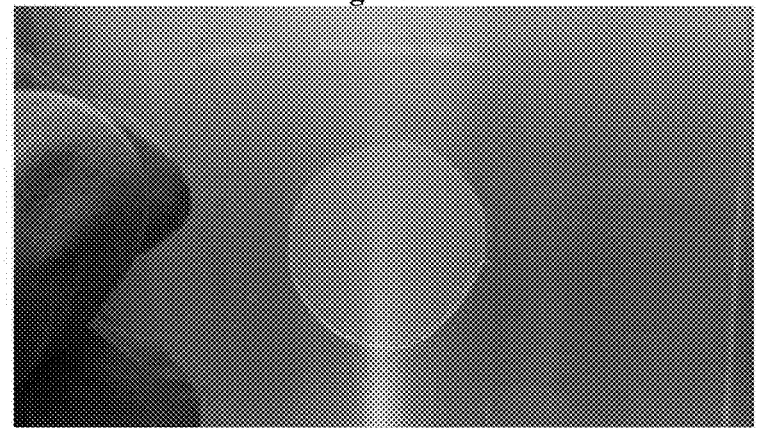
FIG. 21 is a photograph of the collagen hydrogel loaded with human lung fibroblasts after plastic compression in accordance with an exemplary embodiment of the disclosed subject matter.

FIGS. 19A and 19B are diagrams of the collagen hydrogel loaded with human lung fibroblasts arranged in the exemplary setup for plastic compression. FIGS. 20A and 20B are diagrams of the plastic compression being performed on the collagen hydrogel loaded with human lung fibroblasts. As illustrated by FIGS. 20A and 20B, liquid can be squeezed out of the gel slowly, by manually applying pressure with the upper microscope slide. As the layers come closer together, the intervening fluid layer (i.e., liquid that has been squeezed out of the gel) pulls the layers into contact by surface tension as illustrated in FIG. 21. FIG. 21 is a photograph of the collagen hydrogel loaded with human lung fibroblasts after plastic compression. Liquid can be blotted from between the layers by gently tapping on a Kimwipe or other absorbent material. After the liquid (i.e., the cell culture media) has been completely removed by blotting, the gel layer can appear noticeably more white and/or opaque, suggesting the removal of most of the liquid (red hue cell culture medium) during the compression process. The layers can then be separated by immersing the entire apparatus in a PBS bath and allowing the layers to gently separate. The resultant gel layers can be thin stromal tissue constructs that could function as thick, living tissue membranes in multilayer assemblies. These constructs can be durable and highly elastic, capable of being manually stretched with tweezers without tearing. The stromal cells inside the constructs can show high viability following the compression process and the surface of the constructs can be amenable to seeding with monolayers of other cells types, for example endothelial cells, as would be required for using these constructs as membrane-type layers in a multilayer organ-on-a-chip assembly.

Figure 22A:
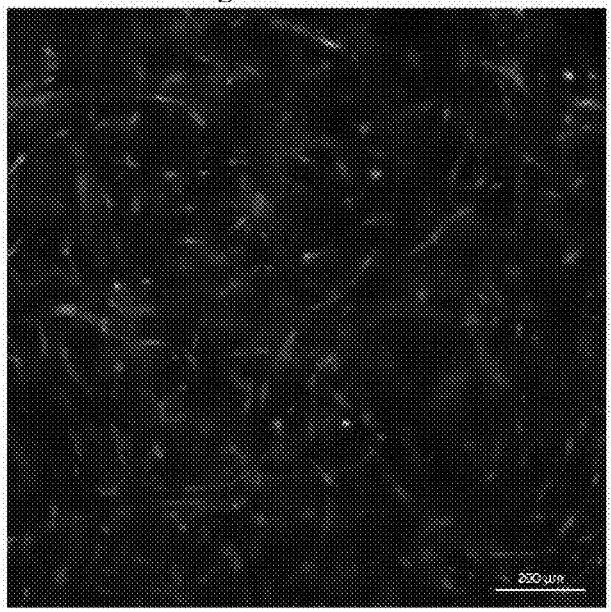
FIGS. 22A-22D illustrate micrographs of exemplary uncompressed lung fibroblast-loaded collagen hydrogel (FIG. 22A), compressed lung fibroblast-loaded collagen hydrogel (FIG. 22B), and the compressed stromal tissue layer subsequently seeded with endothelial cells (FIGS. 22C-22D) in accordance with an exemplary embodiment of the disclosed subject matter.
Figure 22B:
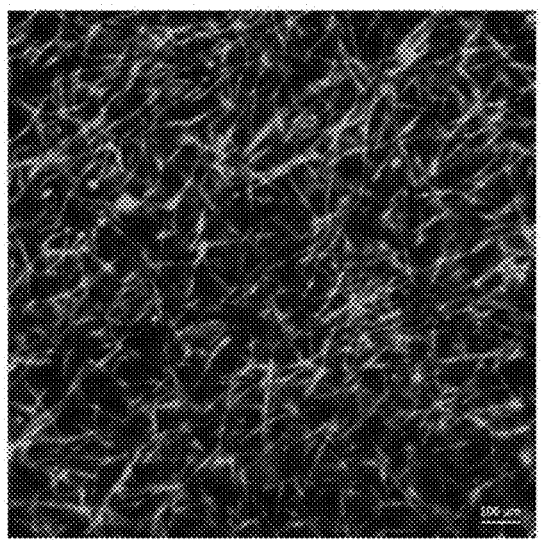
Figure 22C:
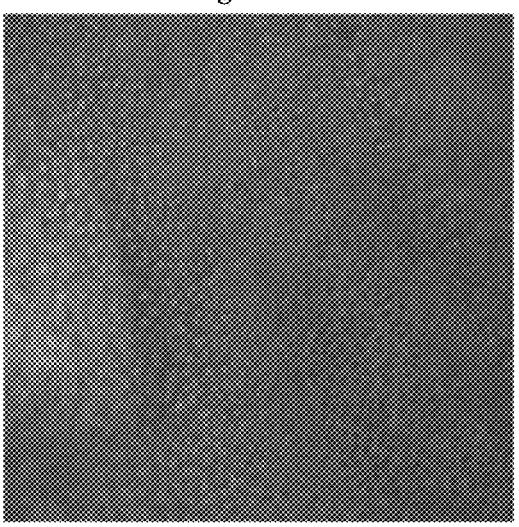
Figure 22D:
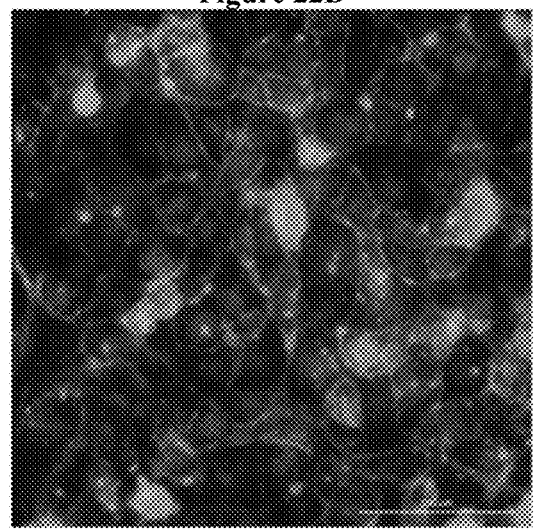

FIGS. 22A-22D illustrate micrographs of exemplary uncompressed lung fibroblast-loaded collagen hydrogels (FIG. 22A), compressed lung fibroblast-loaded collagen hydrogel (FIG. 22B), and the resultant compressed stromal tissue layer subsequently seeded with endothelial cells (FIGS. 22C-22D).

Novel Methods of Sourcing Human ECM Materials for Membrane Fabrication

As the use of human d-ECM and derivative solutions can become prevalent in various biomedical applications, novel approaches can be developed to derive human ECM materials for membrane fabrication from cultured human cells and engineered human microtissues. Two such exemplary approaches are described below.

Figure 23:
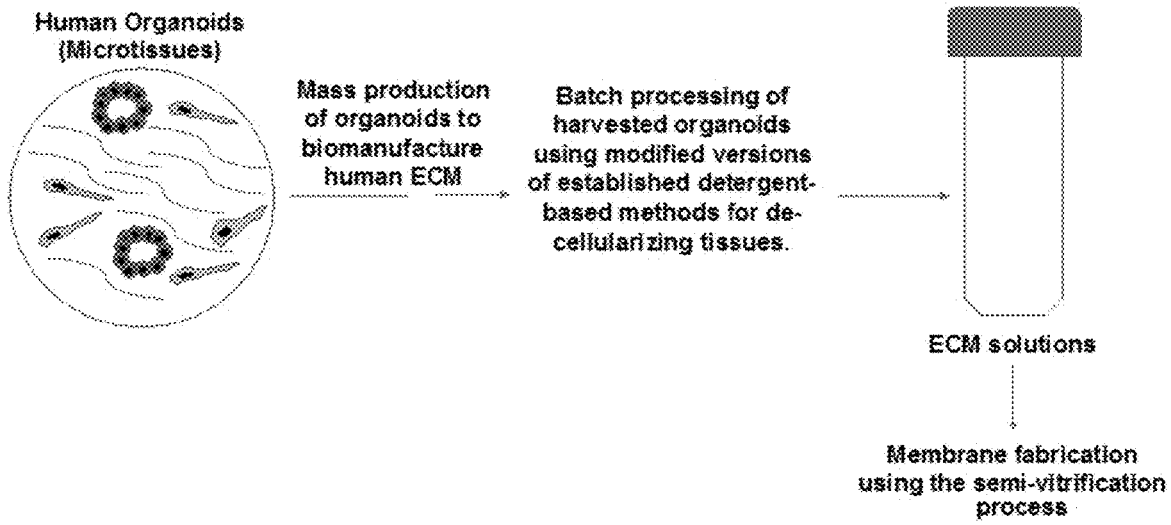
FIG. 23 illustrates an exemplary process for using engineered human microtissues as a source of human ECM materials for membrane fabrication in accordance with an exemplary embodiment of the disclosed subject matter.

Approach #1: Engineered Human Microtissues as a Source of Human ECM Materials for Membrane Fabrication FIG. 23 illustrates an exemplary process for using engineered human microtissues as a source of human ECM materials for membrane fabrication. In some embodiments, human-derived ECM materials used for membrane fabrication can leverage 3-D culture of human cells as organoids wherein the cells produce a complex mixture of endogenous ECM. This process can be used to produce human ECM material, which are generally not available commercially outside of certain exorbitantly expensive ECM proteins. Tissue-specific cells can be used to produce a milieu of ECM that can serve as an application specific source material for membrane fabrication (i.e., production of human liver ECM to fabricate membranes for a liver chip).

In some embodiments, membranes that contain a rich mixture of tissue type-specific ECM can be produced from organoids comprised of cells derived from the tissue of interest. The cells can be transformed lines, primary cells that are amenable to expansion to sufficient numbers or stem/progenitor-derived, (i.e., human iPS-derived tissue cells). The organoids can be comprised of a single cell type or the co-culture ratios can be altered to produce ECM material for fabricating membranes with a cell type-specific ECM composition. Cells of non-human origin can be added to human cell culture in order to increase the rate of ECM production and/or to engineer the type of ECM produced. The organoids can be treated with biochemical agents as a means to control the process of ECM production and deposition. Similarly, the organoids can be subjected to mechanical and/or electrical signals as a way to control the process of ECM production. The organoids can be assembled into more organized structures. Cells and organoids can be encapsulated in 3D matrices to provide additional signals conducive to the synthesis and deposition of ECM. ECM membrane inserts can be developed for multiple tissue types using this method, including pulmonary tissues, hepatic tissue and skeletal muscle among others.

Following an extended culture under conditions optimized to yield the desired composition and amount of ECM, large batches of organoids can be pooled and processed using modified tissue decellularization protocols to remove the cells and harvest the human cell-derived ECM materials. This approach can be particularly robust due to its inherent scalability using bioreactors for batch culture of organoids. In some embodiments, membranes that contain a rich mixture of tissue type-specific ECM can be produced from organoids comprised of cells derived from the tissue of interest. In some embodiments, the cells can be transformed lines, primary cells that are amenable to expansion to sufficient numbers or stem/progenitor-derived (i.e. human iPS-derived tissue cells). In some embodiments, the organoids can be comprised of a single cell type. In some other embodiments, the co-culture ratios can be altered to produce ECM material for fabricating membranes with a cell type-specific ECM composition. In some embodiments, cells of non-human origin can be added to human cell culture to increase the rate of ECM production and/or to engineer the type of ECM produced. In some embodiments, the organoids can be treated with biochemical agents to control the process of ECM production and deposition. Similarly, the organoids can be subjected to mechanical and/or electrical signals to control the process of ECM production. In some embodiments, the organoids can be assembled into more organized structures to facilitate production of even more diverse complements of ECM. In some embodiments, cells and organoids can be encapsulated in 3D matrices to provide additional signals conducive to the synthesis and deposition of ECM. In some embodiments, ECM membrane inserts can be developed for multiple tissue types using this method, including pulmonary tissues, hepatic tissue and skeletal muscle—among others.

Figure 24:
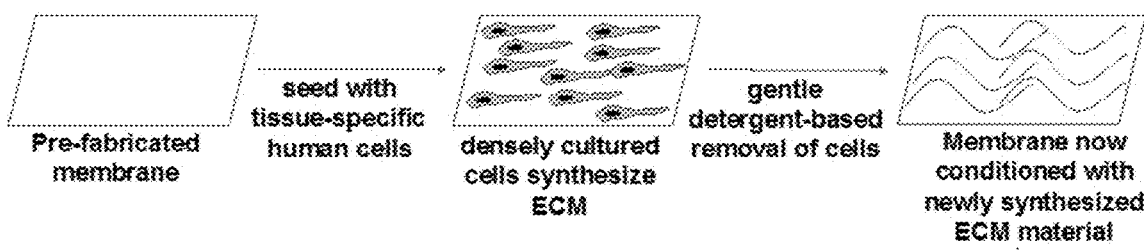
FIG. 24 illustrates an exemplary process for conditioning a pre-fabricated membrane with living human cells to enrich the surface of the pre-fabricated membrane with complements of human ECM proteins in accordance with an exemplary embodiment of the disclosed subject matter.

Approach #2: 'Cyto-Conditioning' of a Pre-Fabricated Membrane Material by Living Human Cells to Enrich the Surface with Unique Complements of Human ECM Proteins Cells derived from a particular tissue of interest are known to produce organ/tissue-specific ECM proteins in culture. FIG. 24 illustrates an exemplary process for conditioning a pre-fabricated membrane with living human cells to enrich the surface of the pre-fabricated membrane with complements of human ECM proteins. Such a process for fabricating organ-specific membrane inserts by utilizing living tissue cells to "cyto-condition" the membrane surface can be followed by gentle detergent removal of the cells and re-drying of the cell-conditioned ECM membrane. In some embodiments, application-specific membrane inserts for multiple tissue types using this method, including pulmonary tissues, hepatic tissue and skeletal muscle can be developed. Membrane inserts fabricated using these approaches can be potentially integral parts of commercially available ready-to-use organ-on-a-chip devices that provide the ideal matrix microenvironment for microfluidic culture of diverse primary human cell types, as well as for differentiation of human stem and progenitor cells.

As show in FIG. 24, the base membrane material can be from a commonly used source (either synthetic or biological material). Living human cells can be used to fabricate the additional ECM surface layers. Although some aspects of FIG. 24's process are similar to that of the process in FIG. 23, in FIG. 24's process the cells can be cultured directly on the membrane to eventually be used where they produce additional surface layers rather than being grown separately as tissues from which ECM can be harvested to fabricate membranes. If the pre-fabricated membrane is produced as a ready to use insert, the product can be ready for drying and storage prior to incorporation in a chip platform by the end user once the membrane has been conditioned with newly synthesized ECM material.

In some embodiments, the cyto-conditioning process illustrated in FIG. 24 can be used to produce membranes with unique ECMs on each surface, for example epithelial-derived on the apical surface and endothelial- or stromal-derived on the basal surface. Simply coating each side of the membrane, even using complex mixtures of multiple ECM proteins, will not provide the breadth of ECM components synthesized by living cells in culture. In some embodiments, optimal cell sources for each type of tissue-specific membrane can be selected and the detergent procedure can be optimized for cellular removal with maximum preservation of the endogenously produced ECM. In some embodiments, robust cell types can be used to produce membranes that facilitate enhanced attachment of fragile primary human cells, as well as enhanced tissue-specific differentiation of progenitor cell types.

In some embodiments, the cells used to cyto-condition the membrane surface with endogenously produced ECM can be transformed lines, primary cells that are amenable to expansion to sufficient numbers or stem/progenitor-derived (i.e. human iPS-derived tissue cells). In some embodiments, the cultured cell layers can be comprised of a single cell type. In some other embodiments, the co-culture ratios can be altered to produce ECM material with cell type-specific ECM composition. Cells of non-human origin can be added to human cell culture to increase the rate of ECM production and/or to engineer the type of ECM produced. The active ECM-producing cultures can be treated with temporal progressions biochemical agents to further refine the process of ECM production and deposition. Similarly, the cultures can be subjected to mechanical and/or electrical signals to control the process of ECM production. In some embodiments, ECM membrane inserts can be developed for multiple tissue types using this method, including pulmonary tissues, hepatic tissue and skeletal muscle.

Product Development

Figure 25:
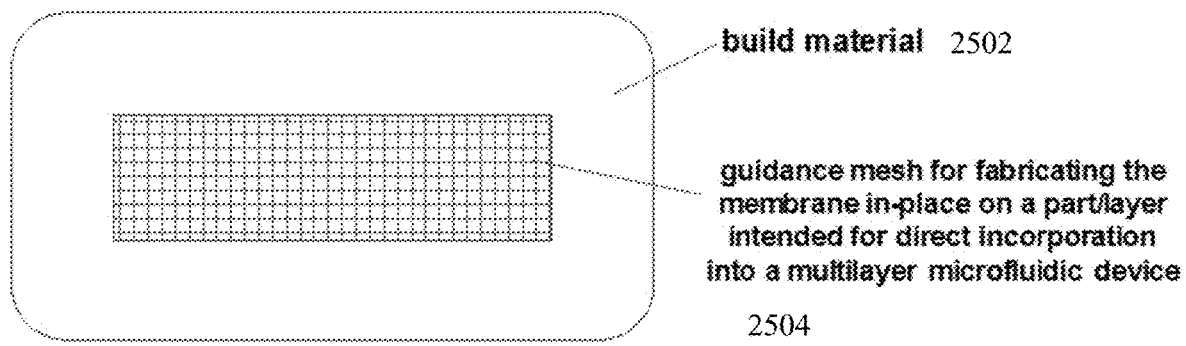
FIG. 25 illustrates an exemplary compartment and buttressing guidance mesh for fabricating and housing the ECM membrane in ready-to-use inserts in accordance with an exemplary embodiment of the disclosed subject matter.

In some embodiments, an exemplary process that leverages human d-ECM solutions derived using Approach #1 can be used to create ready-to-use products in the form of membrane insert layers or thin 3D tissue inserts for multilayer microfluidic device assembly. The exemplary process can involve forming the membrane in a PDMS (and/or other build material) insert that can be customizable and therefore ready-to-bond with the desired multilayer microdevice configuration (as illustrated in FIG. 25). FIG. 25 illustrates an exemplary compartment and buttressing guidance mesh for fabricating and housing the ECM membrane in ready-to-use inserts. As illustrated by FIG. 25, build material 2502 can be fabricated containing a compartment of desired dimensions to house the ECM membrane. This compartment can be in direct apposition to a microfluidic channel and/or multiple channels that are part of the same build layer. Within such a compartment, a mesh 2504 and/or similar buttressing structure, that fabricated from an inert but structurally rigid material (e.g., potentially the device material 2502), can be used to cast the membrane in place and maintain horizontal orientation. A semi-vitrification process can be applied by fabricating the membrane in place on a device layer that is used to assemble a multi-layered device.

In some embodiments, the thickness of membrane can be tunable by repeating the process multiple times to build thicker membranes layer by layer. Using this approach in combination with methods for increasing membrane porosity can facilitate fabrication of 3-D 'tissue inserts' that go beyond providing a partitioning membrane by introducing a 3-D tissue layer with tunable biophysical properties and tissue-specific ECM composition between microfluidic compartments. These 'tissue inserts' can contain living cells and can be fabricated using any of the additional compression-based hydrogel engineering methods described herein.

The present disclosure is well adapted to attain the ends and advantages mentioned as well as those that are inherent therein. The particular embodiments disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above can be altered or modified and all such variations are considered within the scope and spirit of the present disclosure. Various publications, patents and patent application are cited herein, the contents of which are hereby incorporated by reference in their entireties.

The invention claimed is:

1. A microfluidic cell culture device, comprising:
    at least one membrane that is naturally derived and comprises vitrified extracellular matrix (ECM) material, wherein the at least one membrane is uncoated;
    a lower layer comprising a first microchannel on which the at least one membrane is placed;
    an upper layer comprising a second microchannel, wherein the upper layer is bonded directly to a surface of the lower layer around the at least one uncoated membrane; and
    a layer of cells seeded on at least one surface of the at least one uncoated membrane.

2. The microfluidic cell culture device of claim 1, wherein the at least one uncoated membrane comprising the vitrified ECM material resembles fibrous architecture of native basement membranes.

3. The microfluidic cell culture device of claim 1, wherein the vitrified ECM material is integrated into a multilayered microfluidic device mimicking physiological multicellular structures and tissue-tissue interfaces.

4. The microfluidic cell culture device of claim 1, wherein the at least one uncoated membrane is an application-specific membrane generated by isolating and vitrifying ECM components from an application-specific tissue type of interest.

5. The microfluidic cell culture device of claim 1, wherein the vitrified ECM material is derived from at least one of animal tissue and human tissue.

6. The microfluidic cell culture device of claim 1, wherein the vitrified ECM material is formed via evaporation-induced vitrification.

7. The microfluidic cell culture device of claim 1, wherein the vitrified ECM material is generated by
    pooling and processing one or more of engineered tissues and organoids comprising human cells using modified tissue decellularization techniques, the pooling and processing including
    removing cells, and
    harvesting human cell-derived ECM materials.

8. The microfluidic cell culture device of claim 7, wherein cells of non-human origin are added to human cell culture in order to increase the rate of ECM production and to control the type of ECM produced.

9. The microfluidic cell culture device of claim 7, wherein the organoids are treated with biochemical agents to control the process of ECM production and deposition, and wherein the organoids are subjected to mechanical or electrical signals to control ECM production.

10. The microfluidic cell culture device of claim 1, wherein the vitrified ECM material comprises
    (i) collagen type I
    (ii) collagen type I and Matrigel, and/or
    (iii) collagen type I and alginate.

11. The microfluidic cell culture device of claim 8, wherein the at least one uncoated membrane is two or more membranes in a stacked arrangement.

12. The microfluidic cell culture device of claim 1, wherein the at least one surface of the at least one uncoated membrane remains uncoated prior to cell seeding.

13. The microfluidic cell culture device of claim 1, wherein the layer of cells comprises human adenocarcinoma cells.

14. The microfluidic cell culture device of claim 1, wherein
    the vitrified ECM material comprises collagen type I and Matrigel, and
    the layer of cells comprises
        a first layer of cells on a first surface of the at least one uncoated membrane facing the first microchannel of the lower layer, and
        a second layer of cells on a second surface of the at least one uncoated membrane facing the second microchannel of the upper layer.

15. The microfluidic cell culture device of claim 14, wherein the first layer of cells comprises human bronchial epithelial cells and the second layer of cells comprises primary human lung fibroblasts.

16. The microfluidic cell culture device of claim 14, wherein the first layer of cells comprises human bronchial epithelial cells and the second layer of cells comprises human venous endothelial cells.

17. The microfluidic cell culture device of claim 14, wherein the first layer of cells comprises human venous endothelial cells and the second layer of cells comprises primary human lung fibroblasts.

18. The microfluidic cell culture device of claim 1, wherein the vitrified ECM material comprises between about 50% and about 80% collagen type I and between about 20% and about 50% Matrigel.

19. The microfluidic cell culture device of claim 1, wherein the at least one uncoated membrane has a Young's modulus of between about 400 kPa and about 600 kPa.

20. The microfluidic cell culture device of claim 18, wherein the vitrified ECM material comprises about 80% collagen type 1 and about 20% Matrigel.

21. The microfluidic cell culture device of claim 10, wherein the vitrified ECM material comprises collagen type 1 and Matrigel.

22. The microfluidic cell culture device of claim 21, wherein the collagen type I is crosslinked with the Matrigel.

23. The microfluidic cell culture device of claim 1, wherein the at least one uncoated membrane is optically transparent.

* * * * *

UNITED STATES PATENT AND TRADEMARK OFFICE
CERTIFICATE OF CORRECTION

PATENT NO. : 12,180,446 B2
APPLICATION NO. : 16/787275
DATED : December 31, 2024
INVENTOR(S) : Dongeun Huh et al.

It is certified that error appears in the above-identified patent and that said Letters Patent is hereby corrected as shown below:

In the Specification

Under Column no. 7, Line nos. 27-35, Replace:
"In some other embodiments, the ECM membrane and/or thin yet mechanically robust ECM layers can be created using mechanical vibration of hydrogels. In some other embodiments, similar ECM structures can be fabricated by exposure of hydrogels to certain source of thermal, electrical, magnetic, and/or optical energy.
The disclosed fabrication methods can facilitate living cells to be embedded in the hydrogel and can allow the living cells to maintain their viability during the fabrication processes. In some embodiments, the geometry of the resultant tissue structures can be engineered by patterning the location of applied compression. In some embodiments, the disclosed vacuum-based compression can be significantly faster than certain weight-based compression techniques."
With:
--In some other embodiments, the ECM membrane and/or thin yet mechanically robust ECM layers can be created using mechanical vibration of hydrogels. In some other embodiments, similar ECM structures can be fabricated by exposure of hydrogels to certain source of thermal, electrical, magnetic, and/or optical energy.
   The disclosed fabrication methods can facilitate living cells to be embedded in the hydrogel and can allow the living cells to maintain their viability during the fabrication processes. In some embodiments, the geometry of the resultant tissue structures can be engineered by patterning the location of applied compression. In some embodiments, the disclosed vacuum-based compression can be significantly faster than certain weight-based compression techniques.--

Under Column no. 10, Line no. 29, Replace:
"10"
With:
--1I--

Under Column no. 12, Line nos. 20-34, Replace:
"In some embodiments, the basement membrane can be composed of two structurally distinct layers.

Signed and Sealed this
Fourth Day of March, 2025

Coke Morgan Stewart
*Acting Director of the United States Patent and Trademark Office*

CERTIFICATE OF CORRECTION (continued)  Page 2 of 3
U.S. Pat. No. 12,180,446 B2

The first layer can be the basal lamina composed at least of cell adhesion molecules and anchoring filaments that adhere to the basolateral side of cells comprising epithelium, vascular endothelium, peripheral nerve axons, adipose tissue, and muscle. This ultrathin (i.e., <100 nm) layer can be connected to 3D networks of ECM fibers known as the reticular lamina. This specialized zone can serve to anchor the basal lamina to the underlying connective tissue and can serve to compartmentalize different tissue types. As the main ECM component of the
reticular lamina, collagen can form striated fibrils that are assembled in a hierarchical manner to provide structural support to the basement membrane. Since collagen is a major structural protein, collagen type I can be used as a base material for developing a simple and cost-effective method to generate ECM-derived cell culture membranes. FIGS. 2A-2F are images illustrating the appearance, surface structure, and composition of the ECM-derived membranes. FIG. 2A illustrates a digital photo 210 of a COL-MAT membrane 110 held by forceps demonstrating mechanical integrity and transparency. As shown in FIG. 2A, the sequential process of collagen hydrogel dehydration can result in the formation of completely dried planar sheets within 48 hours that can be peeled, trimmed to desired dimensions, and easily handled using fine forceps. With 400 µl of collagen hydrogel uniformly spread over an area of 200 mm$^2$ (10 mm×20 mm), the average thickness of the resulting films can be measured to be 20 µm. The membrane thickness can be adjusted by changing the initial
volume of collagen hydrogel and/or sequentially repeating the same rehydration cycle to deposit additional membrane layers."
With:
--In some embodiments, the basement membrane can be composed of two structurally distinct layers. The first layer can be the basal lamina composed at least of cell adhesion molecules and anchoring filaments that adhere to the basolateral side of cells comprising epithelium, vascular endothelium, peripheral nerve axons, adipose tissue, and muscle. This ultrathin (i.e., <100 nm) layer can be connected to 3D networks of ECM fibers known as the reticular lamina. This specialized zone can serve to anchor the basal lamina to the underlying connective tissue and can serve to compartmentalize different tissue types. As the main ECM component of the reticular lamina, collagen can form striated fibrils that are assembled in a hierarchical manner to provide structural support to the basement membrane. Since collagen is a major structural protein, collagen type I can be used as a base material for developing a simple and cost-effective method to generate ECM-derived cell culture membranes.

FIGS. 2A-2F are images illustrating the appearance, surface structure, and composition of the ECM-derived membranes. FIG. 2A illustrates a digital photo 210 of a COL-MAT membrane 110 held by forceps demonstrating mechanical integrity and transparency. As shown in FIG. 2A, the sequential process of collagen hydrogel dehydration can result in the formation of completely dried planar sheets within 48 hours that can be peeled, trimmed to desired dimensions, and easily handled using fine forceps. With 400 µl of collagen hydrogel uniformly spread over an area of 200 mm$^2$ (10 mm×20 mm), the average thickness of the resulting films can be measured to be 20 µm. The membrane thickness can be adjusted by changing the initial volume of collagen hydrogel and/or sequentially repeating the same rehydration cycle to deposit additional membrane layers.--

Under Column no. 13, Line nos. 7-26, Replace:
"FIG. 2C illustrates SEM visualization of collagen type I and Matrigel composite (COL-MAT) membrane surface ultrastructure having a scale bar of 10 µm. As was the case with the COL membranes, the disclosed technique generated planar collagen-Matrigel (COL-MAT) membranes with similar thickness and structural integrity that consisted of densely packed ECM fibers (as shown in FIG. 2C). FIG. 2D illustrates immunofluorescence staining of laminin protein in COL membranes

CERTIFICATE OF CORRECTION (continued)
U.S. Pat. No. 12,180,446 B2 demonstrates an expected absence of laminin protein. The scale bar in FIG. 2D is 200 μm. FIG. 2E illustrates that immunofluorescence staining of laminin protein in COL-MAT membranes shows robust incorporation of laminin within the fibrous microarchitecture (as shown in inset 208 of FIG. 2E). The scale bar in FIG. 2E is 200 μm. Successful integration of Matrigel components can be evidenced by immunofluorescence detection of laminin in COL-MAT membranes. FIG. 2F illustrates the SEM visualization 220 of Transwell membrane surface ultrastructure having a Transwell insert 212 and showing 400 nm pores and smooth culture surfaces. The scale bar in SEM visualization 220 of FIG. 2F is 10 μm. The biomimetic structure and composition of the disclosed ECM membranes can be in stark contrast to the structure of commercially available Transwell cell culture membranes 216 that showed highly artificial and smooth surfaces with randomly distributed nanoscopic pores."
With:
--FIG. 2C illustrates SEM visualization of collagen type I and Matrigel composite (COL-MAT) membrane surface ultrastructure having a scale bar of 10 μm. As was the case with the COL membranes, the disclosed technique generated planar collagen-Matrigel (COL-MAT) membranes with similar thickness and structural integrity that consisted of densely packed ECM fibers (as shown in FIG. 2C).

FIG. 2D illustrates immunofluorescence staining of laminin protein in COL membranes demonstrates an expected absence of laminin protein. The scale bar in FIG. 2D is 200 μm. FIG. 2E illustrates that immunofluorescence staining of laminin protein in COL-MAT membranes shows robust incorporation of laminin within the fibrous microarchitecture (as shown in inset 208 of FIG. 2E). The scale bar in FIG. 2E is 200 μm. Successful integration of Matrigel components can be evidenced by immunofluorescence detection of laminin in COL-MAT membranes. FIG. 2F illustrates the SEM visualization 220 of Transwell membrane surface ultrastructure having a Transwell insert 212 and showing 400 nm pores and smooth culture surfaces. The scale bar in SEM visualization 220 of FIG. 2F is 10 μm. The biomimetic structure and composition of the disclosed ECM membranes can be in stark contrast to the structure of commercially available Transwell cell culture membranes 216 that showed highly artificial and smooth surfaces with randomly distributed nanoscopic pores.--